US012758646B2

(12) United States Patent
Mettetal, II et al.

(10) Patent No.: US 12,758,646 B2
(45) Date of Patent: Oct. 13, 2026

(54) COMBINATION OF ANTIBODY-DRUG CONJUGATE AND CDK9 INHIBITOR

(71) Applicants: AstraZeneca UK Limited, Cambridge (GB); DAIICHI SANKYO COMPANY, LIMITED, Tokyo (JP)

(72) Inventors: Jerome Thomas Mettetal, II, Wilmington, DE (US); Justin Robert Cidado, Wilmington, DE (US); Scott Boiko, Wilmington, DE (US)

(73) Assignees: AstraZeneca UK Limited, Cambridge (GB); Daiichi Sankyo Company, Limited, Tokyo (JP)

( * ) Notice: Subject to any disclaimer, the term of this patent is extended or adjusted under 35 U.S.C. 154(b) by 703 days.

(21) Appl. No.: 18/012,434

(22) PCT Filed: Jun. 23, 2021

(86) PCT No.: PCT/IB2021/055547
§ 371 (c)(1),
(2) Date: Dec. 22, 2022

(87) PCT Pub. No.: WO2021/260578
PCT Pub. Date: Dec. 30, 2021

(65) Prior Publication Data

US 2023/0233540 A1 Jul. 27, 2023

Related U.S. Application Data

(60) Provisional application No. 63/043,528, filed on Jun. 24, 2020.

(51) Int. Cl.
*A61K 45/06* (2006.01)
*A61K 31/4439* (2006.01)
*A61K 39/00* (2006.01)
*A61K 47/68* (2017.01)
*A61P 35/00* (2006.01)
*C07K 16/28* (2006.01)

(52) U.S. Cl.
CPC ...... *A61K 47/6855* (2017.08); *A61K 31/4439* (2013.01); *A61K 39/001106* (2018.08); *A61K 47/68037* (2023.08); *A61K 47/6889* (2017.08); *A61P 35/00* (2018.01); *C07K 16/2863* (2013.01)

(58) Field of Classification Search
None
See application file for complete search history.

(56) References Cited

U.S. PATENT DOCUMENTS 5,821,337 A 10/1998 Carter et al.

FOREIGN PATENT DOCUMENTS

| | | | | |
|---|---|---|---|---|
| EP | 3101032 A1 * | 12/2016 | ............. A61P 35/00 |
| WO | WO-90/07861 A1 | 7/1990 | |
| WO | WO-99/54342 A1 | 10/1999 | |
| WO | WO-00/61739 A1 | 10/2000 | |
| WO | WO-01/00245 A2 | 1/2001 | |

(Continued)

OTHER PUBLICATIONS

Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, Issue 20, 2016, pp. 5097-5108.

(Continued)

*Primary Examiner* — Kortney L. Klinkel
*Assistant Examiner* — Alison Azar Hastings
(74) *Attorney, Agent, or Firm* — Foley & Lardner LLP

(57) ABSTRACT

A pharmaceutical product for administration of an anti HER2 antibody-drug conjugate in combination with a CDK9 inhibitor is provided. The anti-HER2 antibody-drug conjugate is an antibody-drug conjugate in which a drug linker represented by the following formula (wherein A represents the connecting position to an antibody) is conjugated to an anti-HER2 antibody via a thioether bond. Also provided is a therapeutic use and method wherein the antibody-drug conjugate and the CDK9 inhibitor are administered in combination to a subject: Formula (I):

(I)

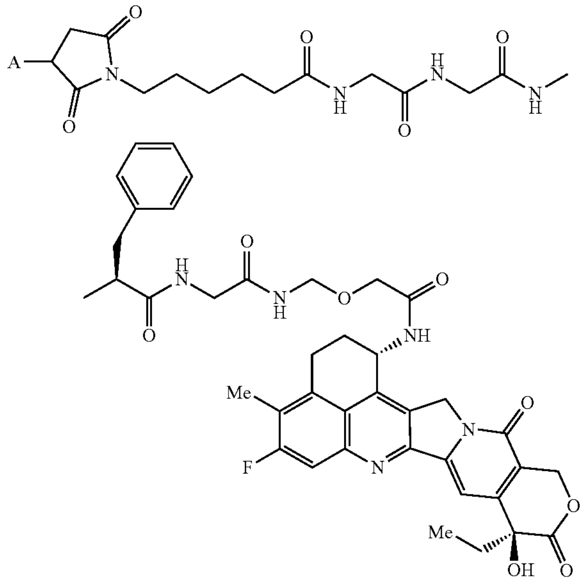

22 Claims, 5 Drawing Sheets

Specification includes a Sequence Listing.

(56) References Cited

FOREIGN PATENT DOCUMENTS

| | | | | | |
|---|---|---|---|---|---|
| WO | WO-02/31140 | A1 | | 4/2002 | |
| WO | WO-2007/133855 | A2 | | 11/2007 | |
| WO | WO-2013/120066 | A1 | | 8/2013 | |
| WO | WO-2014/057687 | A1 | | 4/2014 | |
| WO | WO-2015/098099 | A1 | | 7/2015 | |
| WO | WO-2015/115091 | A1 | | 8/2015 | |
| WO | WO-2015/155998 | A1 | | 10/2015 | |
| WO | WO-2017/002776 | A1 | | 1/2017 | |
| WO | WO-2017001354 | A1 | * | 1/2017 | ........... C07D 487/04 |
| WO | WO-2018/212136 | A1 | | 11/2018 | |
| WO | WO-2019/154177 | A1 | | 8/2019 | |

OTHER PUBLICATIONS

Alley et al., "Antibody-drug conjugates: targeted drug delivery for cancer," Current Opinion in Chemical Biology, vol. 14, 2010, pp. 529-537.

Adams et al., "Structural and functional analysis of the interaction between the agonistic monoclonal antibody Apomab and the proapoptotic receptor DR5," Cell Death & Differentiation, vol. 15, 2008, pp. 751-761.

Austin et al., "Endocytosis and Sorting of ErbB2 and the Site of Action of Cancer Therapeutics Trastuzumab and Geldanamycin," Molecular Biology of the Cell, vol. 15, Issue 12, Dec. 2004, pp. 5268-5282.

Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.

Carmen et al., "Concepts in antibody phage display," Briefings in Functional Genomics and Proteomics, vol. 1, Issue 2, Aug. 2002, pp. 189-203.

Damle, Nitin K., "Tumour-targeted chemotherapy with immunoconjugates of calicheamicin," Expert Opin. Biol. Ther., vol. 4, No. 9, 2004, pp. 1445-1452.

Ducry et al., "Antibody—Drug Conjugates: Linking Cytotoxic Payloads to Monoclonal Antibodies," Bioconjugate Chem, vol. 21, 2010, pp. 5-13.

Harris, Reed J., "Processing of C-terminal lysine and arginine residues of proteins isolated from mammalian cell culture," Journal of Chromatography A, vol. 705, Issue 1, Jun. 23, 1995, pp. 129-134.

Johnson et al., "Cation exchange-HPLC and mass spectrometry reveal C-terminal amidation of an lgG1 heavy chain," Analytical Biochemistry, vol. 360, Issue 1, Jan. 1, 2007, pp. 75-83.

Jones et al., "Replacing the complementarity-determining regions in a human antibody with those from a mouse," Nature, vol. 321, 1986, pp. 522-525.

Kohls et al., "Mab-ZAP: a tool for evaluating antibody efficacy for use in an immunotoxin," BioTechniques, vol. 28, Issue 2, Jan. 2000, pp. 162-165.

Kuroiwa et al., "Efficient modification of a human chromosome by telomere-directed truncation in high homologous recombination-proficient chicken DT40 cells," Nucleic Acids Research, vol. 26, Issue 14, Jul. 1, 1998, pp. 3447-3448.

Morrison et al., "Chimeric human antibody molecules: mouse antigen-binding domains with human constant region domains," Proc. Natl. Acad. Sci. USA., vol. 81, Issue 21, Nov. 1984, pp. 6851-6855.

Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.

Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.

Siriwardena et al., "Human antitransforming growth factor β2 monoclonal antibody—a new modulator of wound healing in trabeculectomy: A randomized placebo controlled clinical study," Ophthalmology, vol. 109, Issue 3, Mar. 2002, pp. 427-431.

Tomizuka et al., "Double trans-chromosomic mice: Maintenance of two individual human chromosome fragments containing Ig heavy and K loci and expression of fully human antibodies," Proc. Natl. Acad. Sci. USA, vol. 97, Issue 2, Jan. 18, 2000, pp. 722-727.

Tomizuka et al., "Functional expression and germline atransmission of a human chromosome fragment in chimaeric mice," Nature Genetics, vol. 16, Jun. 1, 1997, pp. 133-143.

Wormstone et al., "TGF-β2-Induced Matrix Modification and Cell Transdifferentiation in the Human Lens Capsular Bag," Investigative Ophthalmology & Visual Science, vol. 43, Jul. 2002, pp. 2301-2308.

International Searching Authority, "International Search Report," issued in connection with International Patent Application No. PCT/IB2021/055547, dated Oct. 4, 2021.

International Searching Authority, "Written Opinion," issued in connection with International Patent Application No. PCT/IB2021/055547, dated Oct. 4, 2021.

PCT International Preliminary Report on Patentability, dated Dec. 13, 2022, which includes the International Searching Authority, "Written Opinion," issued in connection with International Patent Application No. PCT/IB2021/055547, dated Oct. 4, 2021.

* cited by examiner

[Figure 1]

SEQ ID NO: 1 - Amino acid sequence of a heavy chain of anti-HER2 antibody

EVQLVESGGGLVQPGGSLRLSCAASGFNIKDTYIHWVR
QAPGKGLEWVARIYPTNGYTRYADSVKGRFTISADTSK
NTAYLQMNSLRAEDTAVYYCSRWGGDGFYAMDYWGQGT
LVTVSSASTKGPSVFPLAPSSKSTSGGTAALGCLVKDY
FPEPVTVSWNSGALTSGVHTFPAVLQSSGLYSLSSVVT
VPSSSLGTQTYICNVNHKPSNTKVDKKVEPKSCDKTHT
CPPCPAPELLGGPSVFLFPPKPKDTLMISRTPEVTCVV
VDVSHEDPEVKFNWYVDGVEVHNAKTKPREEQYNSTYR
VVSVLTVLHQDWLNGKEYKCKVSNKALPAPIEKTISKA
KGQPREPQVYTLPPSREEMTKNQVSLTCLVKGFYPSDI
AVEWESNGQPENNYKTTPPVLDSDGSFFLYSKLTVDKS
RWQQGNVFSCSVMHEALHNHYTQKSLSLSPGK

[Figure 2]

SEQ ID NO: 2 - Amino acid sequence of a light chain of anti-HER2 antibody

DIQMTQSPSSLSASVGDRVTITCRASQDVNTAVAWYQQ
KPGKAPKLLIYSASFLYSGVPSRFSGSRSGTDFTLTIS
SLQPEDFATYYCQQHYTTPPTFGQGTKVEIKRTVAAPS
VFIFPPSDEQLKSGTASVVCLLNNFYPREAKVQWKVDN
ALQSGNSQESVTEQDSKDSTYSLSSTLTLSKADYEKHK
VYACEVTHQGLSSPVTKSFNRGEC

[Figure 3]

SEQ ID NO: 3 - Amino acid sequence of heavy chain CDRH1

GFNIKDTY

[Figure 4]

SEQ ID NO: 4 - Amino acid sequence of heavy chain CDRH2

IYPTNGYT

[Figure 5]

SEQ ID NO: 5 - Amino acid sequence of heavy chain CDRH3

S R W G G D G F Y A M D Y

[Figure 6]

SEQ ID NO: 6 - Amino acid sequence of light chain CDRL1

Q D V N T A

[Figure 7]

SEQ ID NO: 7 - Amino acid sequence comprising an amino acid sequence of light chain CDRL2 (SAS)

S A S F L Y S

[Figure 8]

SEQ ID NO: 8 - Amino acid sequence of light chain CDRL3

Q Q H Y T T P P T

[Figure 9]

SEQ ID NO: 9 - Amino acid sequence of heavy chain variable region

E V Q L V E S G G G L V Q P G G S L R L S C A A S G F N I K D T Y I H W V R
Q A P G K G L E W V A R I Y P T N G Y T R Y A D S V K G R F T I S A D T S K
N T A Y L Q M N S L R A E D T A V Y Y C S R W G G D G F Y A M D Y W G Q G T
L V T V S S

[Figure 10]

SEQ ID NO: 10 - Amino acid sequence of light chain variable region

D I Q M T Q S P S S L S A S V G D R V T I T C R A S Q D V N T A V A W Y Q Q
K P G K A P K L L I Y S A S F L Y S G V P S R F S G S R S G T D F T L T I S
S L Q P E D F A T Y Y C Q Q H Y T T P P T F G Q G T K V E I K

[Figure 11]

SEQ ID NO: 11 - Amino acid sequence of heavy chain

E V Q L V E S G G G L V Q P G G S L R L S C A A S G F N I K D T Y I H W V R
Q A P G K G L E W V A R I Y P T N G Y T R Y A D S V K G R F T I S A D T S K
N T A Y L Q M N S L R A E D T A V Y Y C S R W G G D G F Y A M D Y W G Q G T
L V T V S S A S T K G P S V F P L A P S S K S T S G G T A A L G C L V K D Y
F P E P V T V S W N S G A L T S G V H T F P A V L Q S S G L Y S L S S V V T
V P S S S L G T Q T Y I C N V N H K P S N T K V D K K V E P K S C D K T H T
C P P C P A P E L L G G P S V F L F P P K P K D T L M I S R T P E V T C V V
V D V S H E D P E V K F N W Y V D G V E V H N A K T K P R E E Q Y N S T Y R
V V S V L T V L H Q D W L N G K E Y K C K V S N K A L P A P I E K T I S K A
K G Q P R E P Q V Y T L P P S R E E M T K N Q V S L T C L V K G F Y P S D I
A V E W E S N G Q P E N N Y K T T P P V L D S D G S F F L Y S K L T V D K S
R W Q Q G N V F S C S V M H E A L H N H Y T Q K S L S L S P G

[Figure 13]
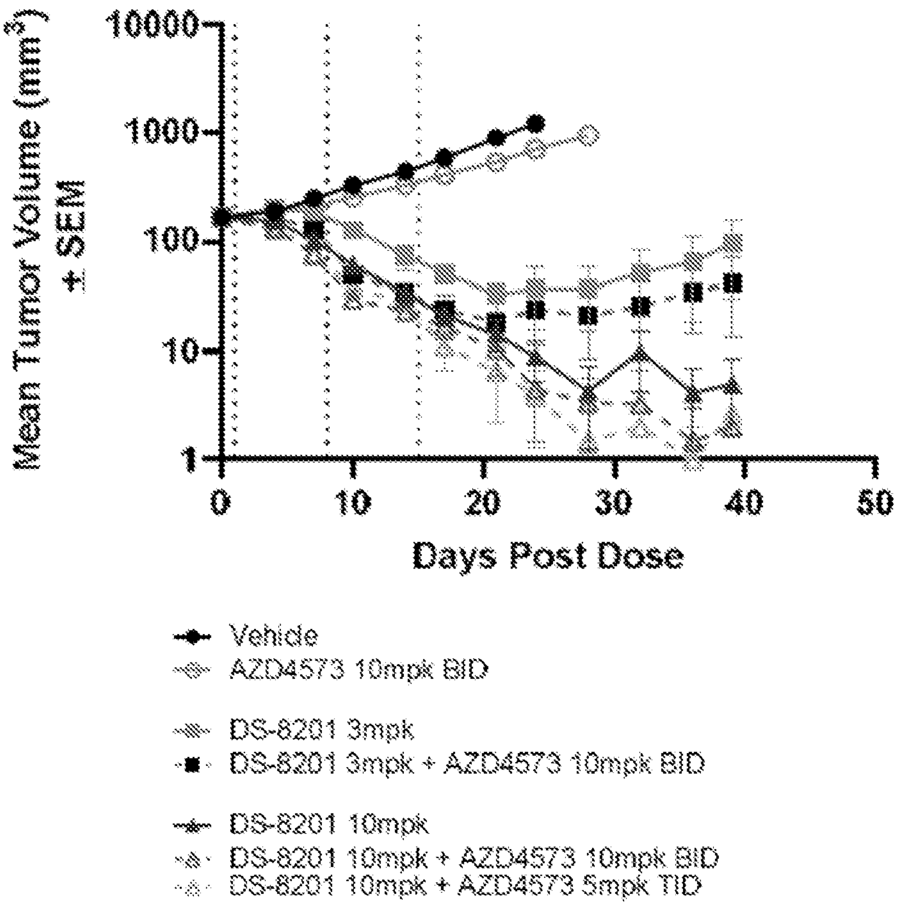

SEQUENCE LISTING

```
<160> NUMBER OF SEQ ID NOS: 11

<210> SEQ ID NO 1
<211> LENGTH: 450
<212> TYPE: PRT
<213> ORGANISM: Artificial Sequence
<220> FEATURE:
```

-continued

<223> OTHER INFORMATION: Heavy chain of humanized anti-HER2 antibody

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

-continued

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 2
<211> LENGTH: 214
<212> TYPE: PRT
<213> ORGANISM: Artificial Sequence
<220> FEATURE:
<223> OTHER INFORMATION: Light chain of humanized anti-HER2 antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 8
<212> TYPE: PRT
<213> ORGANISM: Artificial Sequence
<220> FEATURE:
<223> OTHER INFORMATION: CDRH1 of heavy chain of humanized anti-HER2
      antibody

<400> SEQUENCE: 3

Gly Phe Asn Ile Lys Asp Thr Tyr
1               5
```

-continued

<210> SEQ ID NO 4
<211> LENGTH: 8
<212> TYPE: PRT
<213> ORGANISM: Artificial Sequence
<220> FEATURE:
<223> OTHER INFORMATION: CDRH2 of heavy chain of humanized anti-HER2 antibody

<400> SEQUENCE: 4

```
Ile Tyr Pro Thr Asn Gly Tyr Thr
1               5
```

<210> SEQ ID NO 5
<211> LENGTH: 13
<212> TYPE: PRT
<213> ORGANISM: Artificial Sequence
<220> FEATURE:
<223> OTHER INFORMATION: CDRH3 of heavy chain of humanized anti-HER2 antibody

<400> SEQUENCE: 5

```
Ser Arg Trp Gly Gly Asp Gly Phe Tyr Ala Met Asp Tyr
1               5                   10
```

<210> SEQ ID NO 6
<211> LENGTH: 6
<212> TYPE: PRT
<213> ORGANISM: Artificial Sequence
<220> FEATURE:
<223> OTHER INFORMATION: CDRL1 of light chain of humanized anti-HER2 antibody

<400> SEQUENCE: 6

```
Gln Asp Val Asn Thr Ala
1               5
```

<210> SEQ ID NO 7
<211> LENGTH: 7
<212> TYPE: PRT
<213> ORGANISM: Artificial Sequence
<220> FEATURE:
<223> OTHER INFORMATION: Sequence comprising CDRL2 of light chain of humanized anti-HER2 antibody

<400> SEQUENCE: 7

```
Ser Ala Ser Phe Leu Tyr Ser
1               5
```

<210> SEQ ID NO 8
<211> LENGTH: 9
<212> TYPE: PRT
<213> ORGANISM: Artificial Sequence
<220> FEATURE:
<223> OTHER INFORMATION: CDRL3 of light chain of humanized anti-HER2 antibody

<400> SEQUENCE: 8

```
Gln Gln His Tyr Thr Thr Pro Pro Thr
1               5
```

<210> SEQ ID NO 9
<211> LENGTH: 120
<212> TYPE: PRT
<213> ORGANISM: Artificial Sequence
<220> FEATURE:
<223> OTHER INFORMATION: Variable region of heavy chain of humanized anti-HER2 antibody

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 10
<211> LENGTH: 107
<212> TYPE: PRT
<213> ORGANISM: Artificial Sequence
<220> FEATURE:
<223> OTHER INFORMATION: Variable region of light chain of humanized
      anti-HER2 antibody

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 11
<211> LENGTH: 449
<212> TYPE: PRT
<213> ORGANISM: Artificial Sequence
<220> FEATURE:
<223> OTHER INFORMATION: Heavy chain of humanized anti-HER2 antibody

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

-continued

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

COMBINATION OF ANTIBODY-DRUG CONJUGATE AND CDK9 INHIBITOR

CROSS-REFERENCE TO RELATED APPLICATIONS

The present application claims priority under 35 U.S.C. § 371 to International Patent Application No. PCT/IB2021/055547, filed Jun. 23, 2021, which claims priority to and the benefit of U.S. Provisional Patent Application No. 63/043,528, filed on Jun. 24, 2020. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy is named 122622-0156 SL.txt and is 14 kb in size.

TECHNICAL FIELD

The present disclosure relates to a pharmaceutical product for administration of a specific antibody-drug conjugate, having an antitumor drug conjugated to an anti-HER2 antibody via a linker structure, in combination with a CDK9 inhibitor, and to a therapeutic use and method wherein the specific antibody-drug conjugate and the CDK9 inhibitor are administered in combination to a subject.

BACKGROUND

Cyclin-dependent protein kinases (CDKs) represent a family of serine/threonine protein kinases that become active upon binding to a cyclin regulatory partner. CDK/cyclin complexes were first identified as regulators of cell cycle progression. CDK/cyclin complexes have also been implicated in transcription and mRNA processing. CDK9/PTEFb (positive transcription elongation factor b) phosphorylates the carboxyl-terminal domain (CTD) of the large subunit of RNA polymerase II (RNAP II), predominantly Ser-2, regulating elongation of transcription. Inhibition of CDK9 and transcriptional repression results in the rapid depletion of short lived mRNA transcripts and associated proteins including Mcl1 and c-myc, leading to induction of apoptosis in tumor cells hyper dependent on these survival proteins. Targeting transcriptional CDKs including CDK9, therefore, represents a therapeutic strategy for treating tumor types hyper-dependent on these labile pro-survival proteins including, but not limited to, hematological malignancies such as acute myeloid leukemia, acute lymphocytic leukemia, high risk myelodysplastic syndrome, chronic myelomonocytic leukemia, Richter's syndrome, B-cell non-Hodgkin lymphoma, T-cell non-Hodgkin lymphoma, small lymphocytic lymphoma, multiple myeloma, chronic lymphocytic leukemia, diffuse large B cell lymphoma, Burkitt's lymphoma, follicular lymphoma and solid tumors such as breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, melanoma, neuroblastoma and colon cancer. CDK9 inhibitors may also have therapeutic utility in other disease indications including cardiology, virology, inflammation and pain. CDK9 inhibitors are disclosed, for example, in WO2017/001354.

Antibody-drug conjugates (ADCs) which are composed of a cytotoxic drug conjugated to an antibody, can deliver the drug selectively to cancer cells, and are therefore expected to cause accumulation of the drug within cancer cells and to kill the cancer cells (Ducry, L., et al., Bioconjugate Chem. (2010) 21, 5-13; Alley, S. C., et al., Current Opinion in Chemical Biology (2010) 14, 529-537; Damle N. K. Expert Opin. Biol. Ther. (2004) 4, 1445-1452; Senter P. D., et al., Nature Biotechnology (2012) 30, 631-637; Burris HA., et al., J. Clin. Oncol. (2011) 29(4): 398-405).

One such antibody-drug conjugate is trastuzumab deruxtecan, which is composed of a HER2-targeting antibody and a derivative of exatecan (Ogitani Y. et al., Clinical Cancer Research (2016) 22(20), 5097-5108; Ogitani Y. et al., Cancer Science (2016) 107, 1039-1046).

Despite the therapeutic potential of antibody-drug conjugates and CDK9 inhibitors, no literature is published that describes a test result demonstrating an excellent effect of combined use of the antibody-drug conjugate and a CDK9 inhibitor or any scientific basis suggesting such a test result. Moreover, in the absence of test results, a possibility exists that combined administration of the antibody-drug conjugate together with another cancer treating agent such as a CDK9 inhibitor could lead to negative interactions and/or sub-additive therapeutic outcomes, and thus an excellent or superior effect obtained by such combination treatment could not be expected.

Accordingly, a need remains for improved therapeutic compositions and methods, that can enhance efficacy of existing cancer treating agents, increase durability of therapeutic response and/or reduce dose-dependent toxicity.

SUMMARY OF DISCLOSURE

The antibody-drug conjugate used in the present disclosure (an anti-HER2 antibody-drug conjugate that includes a derivative of the topoisomerase I inhibitor exatecan) has been confirmed to exhibit an excellent antitumor effect in the treatment of certain cancers such as breast cancer and gastric cancer, when administered singly. Furthermore, a CDK9 inhibitor has been confirmed to exhibit an antitumor effect in the treatment of certain cancers. However, it is desired to provide a medicine and treatment which can obtain a superior antitumor effect in the treatment of cancers, such as enhanced efficacy, increased durability of therapeutic response and/or reduced dose-dependent toxicity.

The present disclosure provides a pharmaceutical product which can exhibit an excellent antitumor effect in the treatment of cancers, through administration of an anti-HER2 antibody-drug conjugate in combination with a CDK9 inhibitor. The present disclosure also provides a therapeutic use and method wherein the anti-HER2 antibody-drug conjugate and CDK9 inhibitor are administered in combination to a subject.

Specifically, the present disclosure relates to the following [1] to [61]:

[1] a pharmaceutical product comprising an anti-HER2 antibody-drug conjugate and a CDK9 inhibitor for administration in combination, wherein the anti-HER2 antibody-drug conjugate is an antibody-drug conjugate in which a drug-linker represented by the following formula:

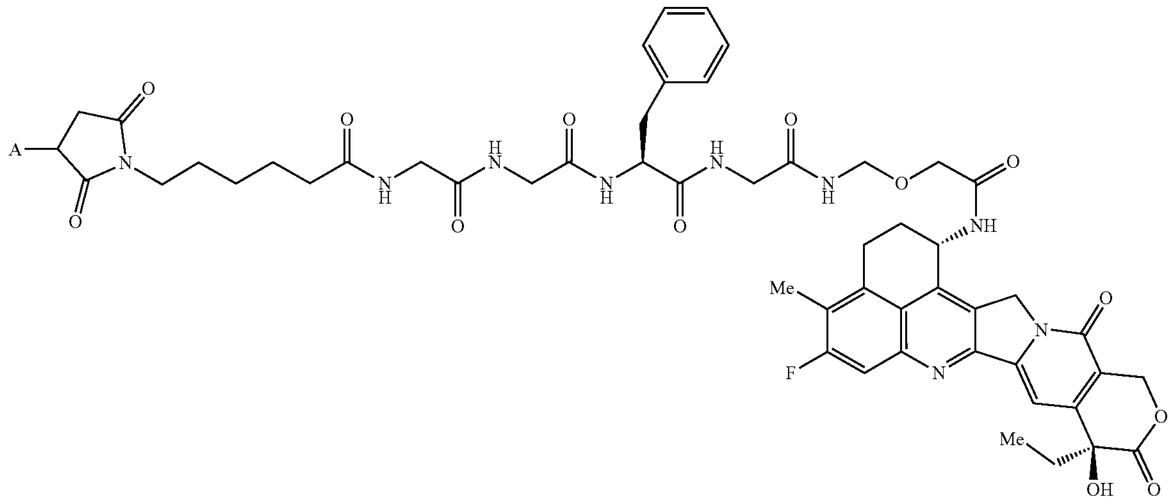

wherein A represents the connecting position to an antibody, is conjugated to an anti-HER2 antibody via a thioether bond;

[2] the pharmaceutical product according to [1], wherein the CDK9 inhibitor is a compound represented by the following formula (I):

(I)

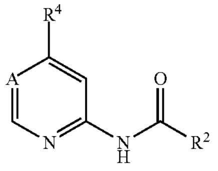

wherein:

A is $C(R^5)$ or N;

$R^5$ is H, $C_{1-3}$ alkyl, CN or halogen;

$R^2$ is 3-7 membered heterocycloalkyl or 3-7 membered cycloalkyl; optionally substituted with one to three substituents independently selected from the group consisting of $R^{10}$, $OR^{10}$, $SR^{10}$, $S(O)\ R^{10}$, $S(O)_2R^{10}$, $C(O)R^{10}$, $C(O)OR^{10}$, $OC(O)R^{10}$, $OC(O)OR^{10}$, $NH_2$, $NHR^{10}$, $N(R^{10})_2$, NHC(O)H, $NHC(O)R^{10}$, $NR^{10}C(O)H$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}O(O)\ NH_2$, $NR^{10}C(O)NHR^{10}$, $NR^{10}C(O)N(R^{10})_2$, $C(O)NH_2$, $C(O)NHR^{10}$, $C(O)N(R^{10})_2$, C(O)NHOH, $C(O)NHOR^{10}$, $C(O)NHS(O)_2R^{10}$, $C(O)\ NR^{10}S(O)_2R^{10}$, $S(O)_2NH_2$, $S(O)_2NHR^{10}$, $S(O)_2N(R^{10})_2$, $S(O)_2NHC(O)\ OR^{10}$, $S(O)_2NR^{10}C(O)\ OR^{10}$, C(O) H, C(O)OH, OH, CN, $NO_2$, F, Cl, Br and I; wherein one or more ring $CH_2$ groups can optionally be replaced by a corresponding number of —C(O) groups, and one or more ring sulfur or nitrogen atoms may be optionally oxidized to form S-oxides or N-oxides;

$R^{10}$, at each occurrence, is independently selected from the group consisting of a 3 to 6 membered cycloalkyl or heterocycloalkyl group, $C_{1-6}$ alkyl, —O—$C_{1-6}$ alkyl, $C_{1-6}$ alkyl-O—$C_{1-6}$ alkyl, $NH_2$, $C(O)NH_2$, C(O)H, C(O)OH, OH, CN, $NO_2$, F, Cl, Br and I; wherein two $R^{10}$ groups together with the atoms to which they are attached may form a 3 to 6 membered cycloalkyl or heterocycloalkyl group; and each aforementioned $R^{10}$ alkyl, cycloalkyl and heterocycloalkyl group may be further substituted with one or two substituents independently selected from CN, OH, halogen, $C_{1-3}$ alkyl, —O—$C_{1-3}$ alkyl, $NH_2$, NH—$C_{1-3}$ alkyl, and NHC(O)—$C_{1-3}$ alkyl;

$R^4$ is

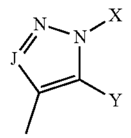

or

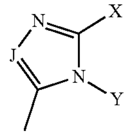

wherein X and Y together with the atoms to which they are attached, form a 5 to 7 membered heterocycloalkyl ring which, in addition to the bridge nitrogen, may contain one or two heteroatoms selected from N, O, and S, which ring may be saturated or partially saturated; wherein one or two ring $CH_2$ groups can optionally be replaced by a corresponding number of —C(O) groups, one or more ring sulfur or nitrogen atoms may be optionally oxidized to form S-oxides or N-oxides and wherein the ring may be substituted on a ring carbon by one or two $R^{10}$ substituents or on a ring nitrogen by an $R^{12}$ substituent;

J is N or $CR^{11}$;

$R^{11}$ is H, $C_{1-3}$ alkyl; and $R^{12}$ is at each occurrence independently selected from the group consisting of a 3 to 6 membered cycloalkyl or heterocycloalkyl group, $C_{1-6}$ alkyl, $C_{1-6}$ alkyl-O—$C_{1-6}$ alkyl, $C(O)NH_2$, C(O)H; wherein each $R^{12}$ alkyl, cycloalkyl and heterocycloalkyl group may be further substituted with one or two substituents independently selected from CN, OH, and halogen, $C_{1-3}$ alkyl, $NH_2$, and NH—$C_{1-3}$ alkyl, NHO(O)—$C_{1-3}$ alkyl, or a pharmaceutical acceptable salt thereof;

[3] the pharmaceutical product according to [2] wherein, in formula (I), A is $C(R^5)$;

[4] the pharmaceutical product according to [3] wherein $R^5$ is chloro;

[5] the pharmaceutical product according to [3] wherein $R^5$ is fluoro;

[6] the pharmaceutical product according to [2] wherein, in formula (I), $R^2$ is a 3-7 membered cycloalkyl;

[7] the pharmaceutical product according to [2] wherein, in formula (I), $R^2$ is 3-7 membered cycloalkyl substituted with $NHCOR^{10}$ or $R^{10}$;

[8] the pharmaceutical product according to [6] wherein $R^2$ is selected from the group cyclopropyl, cyclobutyl, cyclopentyl, cyclohexyl, and cycloheptyl;

[9] the pharmaceutical product according to [8] wherein $R^2$ is selected from the cyclopentyl and cyclohexyl;

[10] the pharmaceutical product according to [7] wherein $R^2$ is cyclohexyl substituted with $NHCOR^{10}$;

[11] the pharmaceutical product according to [2] wherein, in formula (I), $R^2$ is 3-7 membered heterocycloalkyl;

[12] the pharmaceutical product according to [2] wherein, in formula (I), $R^2$ is 3-7 membered heterocycloalkyl substituted with $NHCOR^{10}$;

[13] the pharmaceutical product according to [2] wherein, in formula (I), wherein $R_4$ is

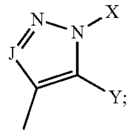

[14] the pharmaceutical product according to [13] wherein J is $C(R^{11})$;

[15] the pharmaceutical product according to [14] wherein $R^{11}$ is H;

[16] the pharmaceutical product according to [2] wherein, in formula (I), X and Y together with the atoms to which they are attached form a 5 membered heterocycloalkyl ring;

[17] the pharmaceutical product according to [2] wherein, in formula (I), X and Y together with the atoms to which they are attached form a 5 membered heterocycloalkyl ring in which one $CH_2$ is substituted with two methyl groups;

[18] the pharmaceutical product according to [2], wherein the CDK9 inhibitor is AZD4573 represented by the following formula:

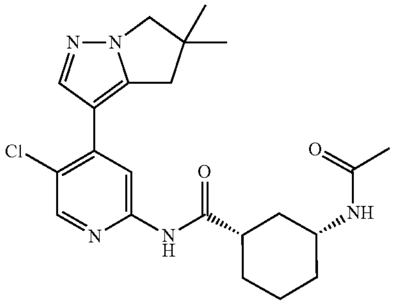 [SMILES: CC(=O)N[C@@H]1CCC[C@H](C(=O)Nc2cc(-c3cnn4c3CC(C)(C)C4)c(Cl)cn2)C1]

or a pharmaceutically acceptable salt thereof;

[19] the pharmaceutical product according to any one of [1] to [18], wherein the anti-HER2 antibody is an antibody comprising a heavy chain comprising CDRH1 consisting of an amino acid sequence represented by SEQ ID NO: 3 [=amino acid residues 26 to 33 of SEQ ID NO: 1], CDRH2 consisting of an amino acid sequence represented by SEQ ID NO: 4 [=amino acid residues 51 to 58 of SEQ ID NO: 1] and CDRH3 consisting of an amino acid sequence represented by SEQ ID NO: 5 [=amino acid residues 97 to 109 of SEQ ID NO: 1], and a light chain comprising CDRL1 consisting of an amino acid sequence represented by SEQ ID NO: 6 [=amino acid residues 27 to 32 of SEQ ID NO: 2], CDRL2 consisting of an amino acid sequence consisting of amino acid residues 1 to 3 of SEQ ID NO: 7 [=amino acid residues 50 to 52 of SEQ ID NO: 2] and CDRL3 consisting of an amino acid sequence represented by SEQ ID NO: 8 [=amino acid residues 89 to 97 of SEQ ID NO: 2];

[20] the pharmaceutical product according to any one of [1] to [18], wherein the anti-HER2 antibody is an antibody comprising a heavy chain comprising a heavy chain variable region consisting of an amino acid sequence represented by SEQ ID NO: 9 [=amino acid residues 1 to 120 of SEQ ID NO: 1] and a light chain comprising a light chain variable region consisting of an amino acid sequence represented by SEQ ID NO: 10 [=amino acid residues 1 to 107 of SEQ ID NO: 2];

[21] the pharmaceutical product according to any one of [1] to [18], wherein the anti-HER2 antibody is an antibody comprising a heavy chain consisting of an amino acid sequence represented by SEQ ID NO: 1 and a light chain consisting of an amino acid sequence represented by SEQ ID NO: 2;

[22] the pharmaceutical product according to any one of [1] to [18], wherein the anti-HER2 antibody is an antibody comprising a heavy chain consisting of an amino acid sequence represented by SEQ ID NO: 11 [=amino acid residues 1 to 449 of SEQ ID NO: 1] and a light chain consisting of an amino acid sequence represented by SEQ ID NO: 2;

[23] the pharmaceutical product according to any one of [1] to [22], wherein the anti-HER2 antibody-drug conjugate is represented by the following formula:

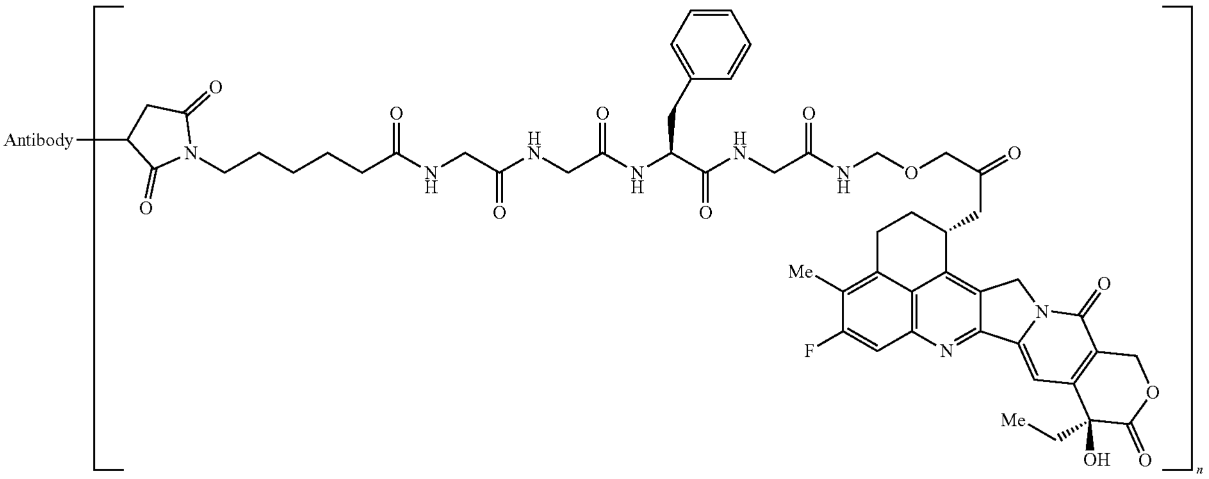

wherein 'Antibody' indicates the anti-HER2 antibody conjugated to the drug-linker via a thioether bond, and n indicates an average number of units of the drug-linker conjugated per antibody molecule in the antibody-drug conjugate, wherein n is in the range of from 7 to 8;

[24] the pharmaceutical product according to any one of [1] to [23], wherein the anti-HER2 antibody-drug conjugate is trastuzumab deruxtecan (DS-8201);

[25] the pharmaceutical product according to any one of [1] to [24] wherein the product is a composition comprising the anti-HER2 antibody-drug conjugate and the CDK9 inhibitor, for simultaneous administration;

[26] the pharmaceutical product according to any one of [1] to [24] wherein the product is a combined preparation comprising the anti-HER2 antibody-drug conjugate and the CDK9 inhibitor, for sequential or simultaneous administration;

[27] the pharmaceutical product according to any one of [1] to [26], wherein the product is for treating cancer;

[28] the pharmaceutical product according to [27], wherein the cancer is at least one selected from the group consisting of breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, melanoma, acute myeloid leukemia, acute lymphocytic leukemia, high risk myelodysplastic syndrome, chronic myelomonocytic leukemia, Richter's syndrome, B-cell non-Hodgkin lymphoma, T-cell non-Hodgkin lymphoma, small lymphocytic lymphoma, multiple myeloma, chronic lymphocytic leukemia, diffuse large B cell lymphoma, Burkitt's lymphoma, and follicular lymphoma;

[29] the pharmaceutical product according to [27], wherein the cancer is breast cancer;

[30] the pharmaceutical product according to [29], wherein the breast cancer has a HER2 status score of IHC 3+;

[31] the pharmaceutical product according to [29], wherein the breast cancer is HER2 low-expressing breast cancer;

[32] the pharmaceutical product according to [29], wherein the breast cancer has a HER2 status score of IHC 2+;

[33] the pharmaceutical product according to [29], wherein the breast cancer has a HER2 status score of IHC 1+;

[34] the pharmaceutical product according to [29], wherein the breast cancer has a HER2 status score of IHC>0 and <1+;

[35] the pharmaceutical product according to [29], wherein the breast cancer is triple-negative breast cancer;

[36] the pharmaceutical product according to [27], wherein the cancer is gastric cancer;

[37] the pharmaceutical product according to [27], wherein the cancer is colorectal cancer;

[38] the pharmaceutical product according to [27], wherein the cancer is lung cancer;

[39] the pharmaceutical product according to [38], wherein the lung cancer is non-small cell lung cancer;

[40] the pharmaceutical product according to [27], wherein the cancer is pancreatic cancer;

[41] the pharmaceutical product according to [27], wherein the cancer is ovarian cancer;

[42] the pharmaceutical product according to [27], wherein the cancer is prostate cancer;

[43] the pharmaceutical product according to [27], wherein the cancer is kidney cancer;

[44] a pharmaceutical product as defined in any one of [1] to [26], for use in treating cancer;

[45] the pharmaceutical product for the use according to [44], wherein the cancer is as defined in any one of [28] to [43];

[46] use of an anti-HER2 antibody-drug conjugate or a CDK9 inhibitor in the manufacture of a medicament for administration of the anti-HER2 antibody-drug conjugate and the CDK9 inhibitor in combination, wherein the anti-HER2 antibody-drug conjugate and the CDK9 inhibitor are as defined in any one of [1] to [24], for treating cancer;

[47] the use according to [46], wherein the cancer is as defined in any one of [28] to [43];

[48] the use according to [46] or [47] wherein the medicament is a composition comprising the anti-HER2 antibody-drug conjugate and the CDK9 inhibitor, for simultaneous administration;

[49] the use according to [46] or [47] wherein the medicament is a combined preparation comprising the anti-HER2 antibody-drug conjugate and the CDK9 inhibitor, for sequential or simultaneous administration;

[50] an anti-HER2 antibody-drug conjugate for use, in combination with a CDK9 inhibitor, in the treatment of cancer, wherein the anti-HER2 antibody-drug conjugate and the CDK9 inhibitor are as defined in any one of [1] to [24];

[51] the anti-HER2 antibody-drug conjugate for the use according to [50], wherein the cancer is as defined in any one of [28] to [43];

[52] the anti-HER2 antibody-drug conjugate for the use according to [50] or [51], wherein the use comprises administration of the anti-HER2 antibody-drug conjugate and the CDK9 inhibitor sequentially;

[53] the anti-HER2 antibody-drug conjugate for the use according to [50] or [51], wherein the use comprises administration of the anti-HER2 antibody-drug conjugate and the CDK9 inhibitor simultaneously;

[54] a CDK9 inhibitor for use, in combination with an anti-HER2 antibody-drug conjugate, in the treatment of cancer, wherein the anti-HER2 antibody-drug conjugate and the CDK9 inhibitor are as defined in any one of [1] to [24];

[55] the CDK9 inhibitor for the use according to [54], wherein the cancer is as defined in any one of [28] to [43];

[56] the CDK9 inhibitor for the use according to [54] or [55], wherein the use comprises administration of the anti-HER2 antibody-drug conjugate and the CDK9 inhibitor sequentially;

[57] the CDK9 inhibitor for the use according to [54] or [55], wherein the use comprises administration of the anti-HER2 antibody-drug conjugate and the CDK9 inhibitor simultaneously;

[58] a method of treating cancer comprising administering an anti-HER2 antibody-drug conjugate and a CDK9 inhibitor as defined in any one of [1] to [24] in combination to a subject in need thereof;

[59] the method according to [58], wherein the cancer is as defined in any one of [28] to [43];

[60] the method according to [58] or [59], wherein the method comprises administering the anti-HER2 antibody-drug conjugate and the CDK9 inhibitor sequentially; and

[61] the method according to [58] or [59], wherein the method comprises administering the anti-HER2 antibody-drug conjugate and the CDK9 inhibitor simultaneously.

Advantageous Effects of Disclosure

The present disclosure provides a pharmaceutical product wherein an anti-HER2 antibody-drug conjugate, having an antitumor drug conjugated to an anti-HER2 antibody via a linker structure, and a CDK9 inhibitor are administered in combination, and a therapeutic use and method wherein the specific antibody-drug conjugate and the CDK9 inhibitor are administered in combination to a subject. Thus, the present disclosure can provide a medicine and treatment which can obtain a superior antitumor effect in the treatment of cancers.

BRIEF DESCRIPTION OF DRAWINGS

FIG. 1 is a diagram showing the amino acid sequence of a heavy chain of an anti-HER2 antibody (SEQ ID NO: 1).

FIG. 2 is a diagram showing the amino acid sequence of a light chain of an anti-HER2 antibody (SEQ ID NO: 2).

FIG. 3 is a diagram showing the amino acid sequence of a heavy chain CDRH1 (SEQ ID NO: 3 [=amino acid residues 26 to 33 of SEQ ID NO: 1]).

FIG. 4 is a diagram showing the amino acid sequence of a heavy chain CDRH2 (SEQ ID NO: 4 [=amino acid residues 51 to 58 of SEQ ID NO: 1]).

FIG. 5 is a diagram showing the amino acid sequence of a heavy chain CDRH3 (SEQ ID NO: 5 [=amino acid residues 97 to 109 of SEQ ID NO: 1]).

FIG. 6 is a diagram showing the amino acid sequence of a light chain CDRL1 (SEQ ID NO: 6 [=amino acid residues 27 to 32 of SEQ ID NO: 2]).

FIG. 7 is a diagram showing an amino acid sequence comprising the amino acid sequence of a light chain CDRL2 (SAS) (SEQ ID NO: 7 [=amino acid residues 50 to 56 of SEQ ID NO: 2]).

FIG. 8 is a diagram showing the amino acid sequence of a light chain CDRL3 (SEQ ID NO: 8 [=amino acid residues 89 to 97 of SEQ ID NO: 2]).

FIG. 9 is a diagram showing the amino acid sequence of a heavy chain variable region (SEQ ID NO: 9 [=amino acid residues 1 to 120 of SEQ ID NO: 1]).

FIG. 10 is a diagram showing the amino acid sequence of a light chain variable region (SEQ ID NO: 10 [=amino acid residues 1 to 107 of SEQ ID NO: 2]).

FIG. 11 is a diagram showing the amino acid sequence of a heavy chain (SEQ ID NO: 11 [=amino acid residues 1 to 449 of SEQ ID NO: 1]).

FIG. 13 is a diagram showing change in tumour volume over time for treatment groups of CB17-SCID mice having HCC12945 breast cancer cells implanted subcutaneously, treated with DS-8201 at 3 mg/kg or 10 mg/kg alone and in combination with AZD4573 at 10 mg/kg BID or 5 mg/kg TID.

Figure 12:
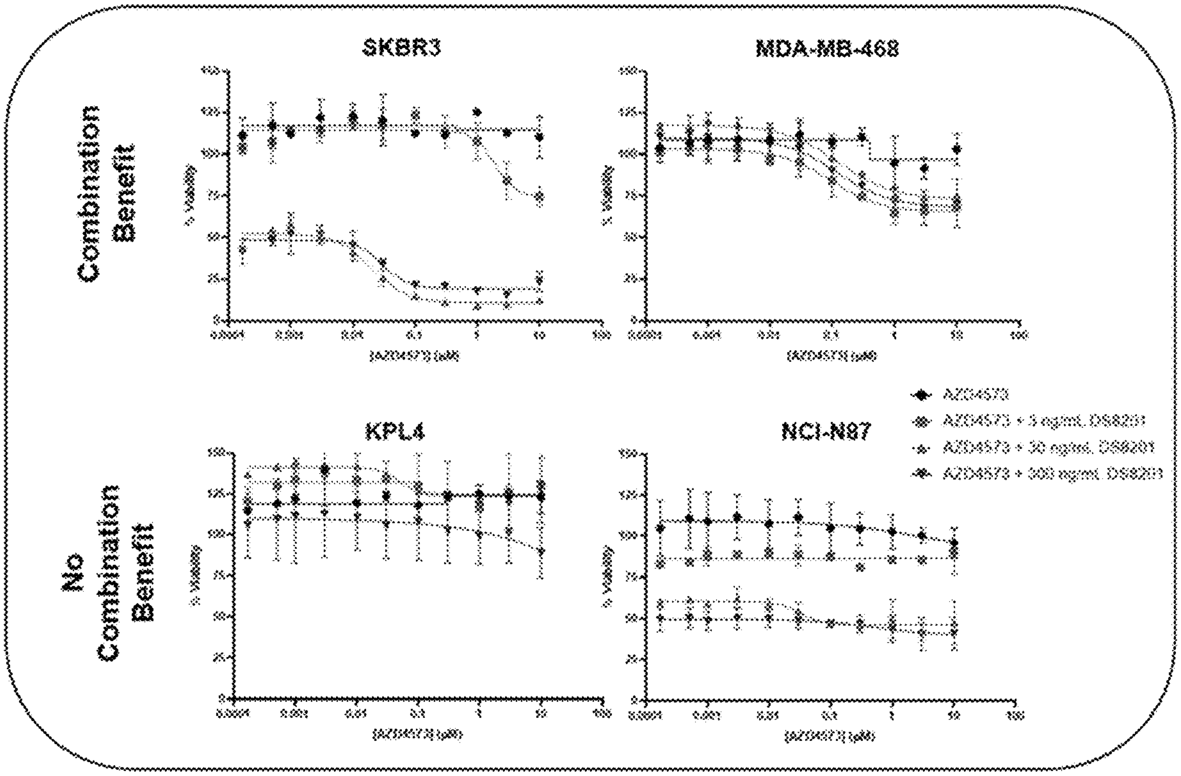
FIG. 12 is a diagram showing dose-response curves for a selective CDK9 inhibitor AZD4573 in combination with increasing doses of an anti-HER2 antibody-drug conjugate DS-8201 in breast and gastric cancer cell lines.

In order that the present disclosure can be more readily understood, certain terms are first defined. Additional definitions are set forth throughout the detailed description.

Before describing the present disclosure in detail, it is to be understood that this disclosure is not limited to specific compositions or method steps, as such can vary. As used in this specification and the appended claims, the singular forms “a”, “an” and “the” include plural referents unless the context clearly dictates otherwise. The terms “a” (or “an”), as well as the terms “one or more,” and “at least one” can be used interchangeably herein.

Furthermore, “and/or” where used herein is to be taken as specific disclosure of each of the two specified features or components with or without the other. Thus, the term “and/or” as used in a phrase such as “A and/or B” herein is intended to include “A and B,” “A or B,” “A” (alone), and “B” (alone). Likewise, the term “and/or” as used in a phrase such as “A, B, and/or C” is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range.

It is understood that wherever aspects are described herein with the language "comprising", otherwise analogous aspects described in terms of "consisting of" and/or "consisting essentially of" are also provided. The terms "inhibit", "block", and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical product" refers to a preparation which is in such form as to permit the biological activity of the active ingredients, either as a composition containing all the active ingredients (for simultaneous administration), or as a combination of separate compositions (a combined preparation) each containing at least one but not all of the active ingredients (for administration sequentially or simultaneously), and which contains no additional components which are unacceptably toxic to a subject to which the product would be administered. Such product can be sterile. By "simultaneous administration" is meant that the active ingredients are administered at the same time. By "sequential administration" is meant that the active ingredients are administered one after the other, in either order, at a time interval between the individual administrations. The time interval can be, for example, less than 24 hours, preferably less than 6 hours, more preferably less than 2 hours.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, breast cancer, gastric cancer, colorectal cancer, lung cancer, esophageal cancer, head-and-neck cancer, esophagogastric junction adenocarcinoma, biliary tract cancer, Paget's disease, pancreatic cancer, ovarian cancer, uterine carcinosarcoma, urothelial cancer, prostate cancer, bladder cancer, gastrointestinal stromal tumor, digestive tract stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, melanoma, acute myeloid leukemia, acute lymphocytic leukemia, high risk myelodysplastic syndrome, chronic myelomonocytic leukemia, Richter's syndrome, B-cell non-Hodgkin lymphoma, T-cell non-Hodgkin lymphoma, small lymphocytic lymphoma, multiple myeloma, chronic lymphocytic leukemia, diffuse large B cell lymphoma, Burkitt's lymphoma, and follicular lymphoma. Cancers include hematological malignancies such as acute myeloid leukemia, multiple myeloma, chronic lymphocytic leukemia, diffuse large B cell lymphoma, Burkitt's lymphoma, follicular lymphoma and solid tumors such as breast cancer, lung cancer, neuroblastoma and colon cancer.

The term "cytotoxic agent" as used herein is defined broadly and refers to a substance that inhibits or prevents the function of cells and/or causes destruction of cells (cell death), and/or exerts anti-neoplastic/anti-proliferative effects. For example, a cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, as well as other HER2 antagonists, anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds.

In accordance with the methods or uses of the present disclosure, compounds of the present disclosure may be administered to a patient to promote a positive therapeutic response with respect to cancer. The term "positive therapeutic response" with respect to cancer treatment refers to an improvement in the symptoms associated with the disease. For example, an improvement in the disease can be characterized as a complete response. The term "complete response" refers to an absence of clinically detectable disease with normalization of any previous test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of compounds of the present disclosure. In specific aspects, such terms refer to one, two or three or more results following the administration of compounds of the instant disclosure:

(1) a stabilization, reduction or elimination of the cancer cell population;
(2) a stabilization or reduction in cancer growth;
(3) an impairment in the formation of cancer;
(4) eradication, removal, or control of primary, regional and/or metastatic cancer;
(5) a reduction in mortality;
(6) an increase in disease-free, relapse-free, progression-free, and/or overall survival, duration, or rate;
(7) an increase in the response rate, the durability of response, or number of patients who respond or are in remission;
(8) a decrease in hospitalization rate,
(9) a decrease in hospitalization lengths,
(10) the size of the cancer is maintained and does not increase or increases by less than 10%, preferably less than 5%, preferably less than 4%, preferably less than 2%, and
(11) an increase in the number of patients in remission.
(12) a decrease in the number of adjuvant therapies (e.g., chemotherapy or hormonal therapy) that would otherwise be required to treat the cancer.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy can experience the beneficial effect of an improvement in the symptoms associated with the disease.

In this specification the prefix $C_{x-y}$ as used in terms such as $C_{x-y}$ alkyl and the like (where x and y are integers) indicates the numerical range of carbon atoms that are present in the group; for example, $C_{1-4}$ alkyl includes $C_1$ alkyl (methyl), $C_2$ alkyl (ethyl), $C_3$ alkyl (propyl and isopropyl) and $C_4$ alkyl (butyl, 1-methylpropyl, 2-methylpropyl, and t-butyl).

Unless specifically stated, the bonding atom of a group may be any suitable atom of that group; for example, propyl includes prop-1-yl and prop-2-yl.

As used herein, the phrase "optionally substituted" indicates that substitution is optional and therefore it is possible for the designated group to be either substituted or unsubstituted. In the event a substitution is desired, any number of hydrogens on the designated group may be replaced with a selection from the indicated substituents, provided that the normal valency of the atoms on a particular substituent is not exceeded, and that the substitution results in a stable compound. In one aspect, when a particular group is designated as being optionally substituted with "one or more" substituents, the particular group may be unsubstituted. In another aspect, the particular group may bear one substituent. In another aspect, the particular substituent may bear two substituents. In still another aspect, the particular group may bear three substituents. In yet another aspect, the particular group may bear four substituents. In a further aspect, the particular group may bear one or two substituents. In still a further aspect, the particular group may be unsubstituted, or may bear one or two substituents.

As used herein the term "alkyl" refers to both straight and branched chain saturated hydrocarbon radicals having the specified number of carbon atoms. References to individual alkyl groups such as "propyl" are specific for the straight chain version only and references to individual branched chain alkyl groups such as "isopropyl" are specific for the branched chain version only. In one aspect, "alkyl" may be "$C_{1-4}$ alkyl". In another aspect, "alkyl" and "$C_{1-4}$ alkyl" may be "$C_{1-3}$ alkyl". In another aspect, "alkyl", "$C_{1-4}$ alkyl" and "$C_{1-3}$ alkyl" may be methyl. An analogous convention applies to other generic terms, for example "alkenyl" and "alkynyl".

"Cycloalkyl" is a monocyclic, saturated or partially unsaturated alkyl ring containing 3 to 7 carbon atoms. Illustrative examples of cycloalkyl include cyclopropyl, cyclobutyl, cyclopentyl, cyclohexyl and cycloheptyl.

"Heterocycloalkyl" is a saturated or partially saturated monocyclic ring containing 3 to 7 ring atoms of which 1, 2, 3 or 4 ring atoms are chosen from nitrogen, sulphur or oxygen, which ring may be carbon or nitrogen linked, wherein a —$CH_2$— group can optionally be replaced by a —C(O)—; wherein a ring nitrogen or sulphur atom is optionally oxidised to form the N-oxide or S-oxide(s) (i.e. sulfoxide and sulfone); wherein a ring —NH is optionally substituted by acetyl, formyl, methyl or mesyl; and wherein a ring is optionally substituted by one or more halo. Illustrative examples of "5- or 6-membered heterocycloalkyl" include, imidazolinyl, pyrazolidinyl, piperazinyl, piperidinyl, pyrrolidinyl, oxazinyl, morpholinyl, hexahydropyrimidinyl, and thiomorpholinyl.

Suitable values for any R group ($R^1$ to $R^{12}$) or any part or substituent for such groups include:

for $C_{1-4}$ alkyl: methyl, ethyl, propyl, isopropyl, butyl, 2-methylpropyl and tert-butyl;
for $C_{1-6}$ alkyl: $C_{1-4}$ alkyl, pentyl, 2,2-dimethylpropyl, 3-methylbutyl and hexyl;
for $C_{3-7}$cycloalkyl: cyclopropyl, cyclobutyl, cyclopentyl cyclohexyl, and cycloheptyl;
for halo or halogen: fluoro, chloro, bromo and iodo;
for heterocycloalkyl: pyrrolidinyl, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, pyranyl, dihydro-2H-pyranyl, tetrahydrofuranyl, 2,5-dioxoimidazolidinyl, and 2,2-dimethyl-1,3-dioxolanyl. It should be noted that examples given for terms used in the description are not limiting.

As used herein, the phrase "effective amount" means an amount of a compound or composition which is sufficient enough to significantly and positively modify the symptoms and/or conditions to be treated (e.g., provide a positive clinical response). The effective amount of an active ingredient for use in a pharmaceutical product will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician. In particular, an effective amount of a compound of formula (I) for use in the treatment of cancer in combination with the antibody-drug conjugate is an amount such that the combination is sufficient to symptomatically relieve in a warm-blooded animal such as man, the symptoms of cancer, to slow the progression of cancer, or to reduce in patients with symptoms of cancer the risk of getting worse.

As used herein, the term "pharmaceutically acceptable" refers to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

With reference to substituent "R" for illustrative purposes, the following substituent definitions refer to the indicated structure:

$-N(R)_2$ = 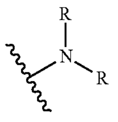 -OR = 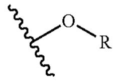

Within the present disclosure it is to be understood that a compound of formula (I) or a salt thereof may exhibit the phenomenon of tautomerism and that the formulae drawings within this specification can represent only one of the possible tautomeric forms. It is to be understood that the disclosure encompasses any tautomeric form which has CDK9 inhibitory activity and is not to be limited merely to any one tautomeric form utilised within the formulae drawings.

It will be understood that compounds of formula (I) may encompass compounds with one or more isotopic substitutions. For example, H may be in any isotopic form, including $^{1}H$, $^{2}H$ (D), and $^{3}H$ (T); C may be in any isotopic form, including $^{12}C$, $^{13}C$, and $^{14}C$; O may be in any isotopic form, including $^{16}O$ and $^{18}O$; and the like.

It is also to be understood that certain compounds of formula (I) and salts thereof can exist in solvated as well as unsolvated forms such as, for example, hydrated forms. It is to be understood that the disclosure encompasses all such solvated forms.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid. Suitable pharmaceutically acceptable esters for carboxy include $C_{1-6}$ alkoxymethyl esters for example methoxymethyl, $C_{1-6}$ alkanoyloxymethyl esters for example pivaloyloxymethyl, phthalidyl esters, $C_{3-8}$ cycloalkcarbonyloxy$C_{1-6}$ alkyl esters for example 1-cyclohexylcarbonyloxyethyl, (1,3-dioxolen-2-one)ylmethyl esters for example (5-methyl-1,3-dioxolen-2-one)ylmethyl, and $C_{1-6}$ alkoxycarbonyloxyethyl esters for example 1-methoxycarbonyloxyethyl; and may be formed at any carboxy group in the compounds of this disclosure. Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy groups. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example acetyl, benzoyl, phenylacetyl, substituted benzoyl and phenylacetyl; $C_{1-10}$ alkoxycarbonyl (to give alkyl carbonate esters), for example ethoxycarbonyl; di-$C_{1-4}$ alkylcarbamoyl and N-(di-$C_{1-4}$ alkylaminomethyl)-N—$C_{1-4}$ alkylcarbamoyl (to give carbamates); di-$C_{1-4}$ alkylaminoacetyl and carboxyacetyl. Examples of ring substituents on phenylacetyl and benzoyl include aminomethyl, $C_{1-4}$ alkylaminomethyl and di-($C_{1-4}$ alkyl)aminomethyl, and morpholino or piperazino linked from a ring nitrogen atom via a methylene linking group to the 3- or 4-position of the benzoyl ring. Other interesting in vivo hydrolysable esters include, for example, $R^{A}C(O)OC_{1-6}$ alkyl-CO—, wherein $R^{A}$ is for example, benzyloxy-$C_{1-4}$ alkyl, or phenyl. Suitable substituents on a phenyl group in such esters include, for example, 4-$C_{1-4}$ alkylpiperazino-$C_{1-4}$ alkyl, piperazino-$C_{1-4}$ alkyl and morpholino-$C_{1-4}$ alkyl.

Compounds of formula (I) may form stable pharmaceutically acceptable acid or base salts, and in such cases administration of a compound as a salt may be appropriate. Examples of acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Examples of base salts include ammonium salts; alkali metal salts such as sodium, lithium and potassium salts; alkaline earth metal salts such as aluminum, calcium and magnesium salts; salts with organic bases such as dicyclohexylamine salts and N-methyl-d-glucamine; and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates such as dimethyl, diethyl, dibutyl; diamyl sulfates; long chain halides such as decyl, lauryl, myristyl and stearyl halides; arylalkyl halides such as benzyl bromide and others. Non-toxic physiologically-acceptable salts are preferred, although other salts may be useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Compounds of formula (I) have chiral centers, and thus exist as stereoisomers. It is to be understood that the disclosure encompasses all such stereoisomers, including enantiomers and diastereoisomers. Insofar as compounds of formula (I) may exist in optically active or racemic forms, the disclosure includes in its definition any such optically active or racemic form which possesses the above-mentioned activity. The present disclosure encompasses all such stereoisomers having activity as herein defined.

The synthesis of optically active forms may be carried out by standard techniques of organic chemistry well known in the art, for example by synthesis from optically active starting materials or by resolution of a racemic form. Racemates may be separated into individual enantiomers using known procedures (see, for example, Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species. Similarly, the above-mentioned activity may be evaluated using standard laboratory techniques.

Thus, throughout the specification, where reference is made to the compound of formula (I), it is to be understood that the term compound includes stereoisomers, mixtures of stereoisomers, and polymorphs that inhibit CDK9 activity in a human or animal.

Stereoisomers may be separated using conventional techniques, e.g. chromatography or fractional crystallisation. The enantiomers may be isolated by separation of a racemate for example by fractional crystallisation, resolution or HPLC. The diastereoisomers may be isolated by separation by virtue of the different physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent.

When a specific stereoisomer is provided (whether provided by separation, by chiral synthesis, or by other methods) it is favorably provided substantially isolated from other stereoisomers of the same compound. In one aspect, a mixture containing a particular stereoisomer of a compound of formula (I) may contain less than 30%, particularly less than 20%, and more particularly less than 10% by weight of other stereoisomer(s) of the same compound. In another aspect, a mixture containing a particular stereoisomer of a compound of formula (I) may contain less than 6%, particularly less than 3%, and more particularly less than 2% by weight of other stereoisomer(s) of the compound. In another aspect, a mixture containing a particular stereoisomer of a compound of formula (I) may contain less than 1%, particularly less than 0.5%, and more particularly less than 0.3%, and still more particularly less than 0.1% by weight of other stereoisomer(s) of the compound. Where the absolute configuration of isolated stereoisomers is not determined, stereoisomers may be differentiated by a method of preparation or separation. For example, isolated stereoisomers may be differentiated by their elution time and denoted, for example, isomer 1, isomer 2, etc.

Some structural forms of the disclosure may provide advantages. For instance, some forms of compound of the disclosure may be easier to handle and store. Other forms of the compound of the disclosure may be easier to characterize because it exists in a well defined state. Additionally, the compound of the disclosure may be easier to synthesize in a reproducible manner and thereby easier to handle in a full scale production.

When a specific polymorphic form is provided, it is favorably provided substantially isolated from other polymorphic forms of the same compound. In one aspect, a mixture containing a particular polymorphic form of a compound of formula (I) may contain less than 30%, particularly less than 20%, and more particularly less than 10% by weight of other polymorphic forms of the same compound. In another aspect, a mixture containing a particular polymorphic form of a compound of formula (I) may contain less than 6%, particularly less than 3%, and more particularly less than 2% by weight of other polymorphic forms of the compound. In another aspect, a mixture containing a particular polymorphic form of a compound of formula (I) may contain less than 1%, particularly less than 0.5%, and more particularly less than 0.3%, and still more particularly less than 0.1% by weight of other polymorphic forms of the compound.

The CDK9 inhibitors herein disclosed may be characterized by the positions and intensities of the major peaks in the X-ray powder diffractogram, but may also be characterized by conventional FT-IR spectroscopy. These may be used to distinguish one crystal form from other crystal forms of the compound. CDK9 inhibitors herein disclosed may be characterized by being highly crystalline, i.e. having a higher crystallinity than other forms. With the expression "any other form" is meant anhydrates, hydrates, solvates, and polymorphs or amorphous forms thereof disclosed in the prior art. Examples of any other forms of compounds include, but are not limited to, anhydrates, monohydrates, dihydrates, sesquihydrates, trihydrates, alcoholates, such as methanolates and ethanolates, and polymorphs or amorphous forms thereof.

The compound of formula (I) may also be characterized by its unit cell. The compound of formula (I) may be analyzed by XRPD, a technique which is known per se.

The amount of water in the compound can be determined by thermogravimetric analysis, a technique which is known per se.

DESCRIPTION OF EMBODIMENTS

Hereinafter, preferred modes for carrying out the present disclosure are described. The embodiments described below are given merely for illustrating one example of a typical embodiment of the present disclosure and are not intended to limit the scope of the present disclosure.

1. Antibody-Drug Conjugate

The antibody-drug conjugate used in the present disclosure is an antibody-drug conjugate in which a drug-linker represented by the following formula:

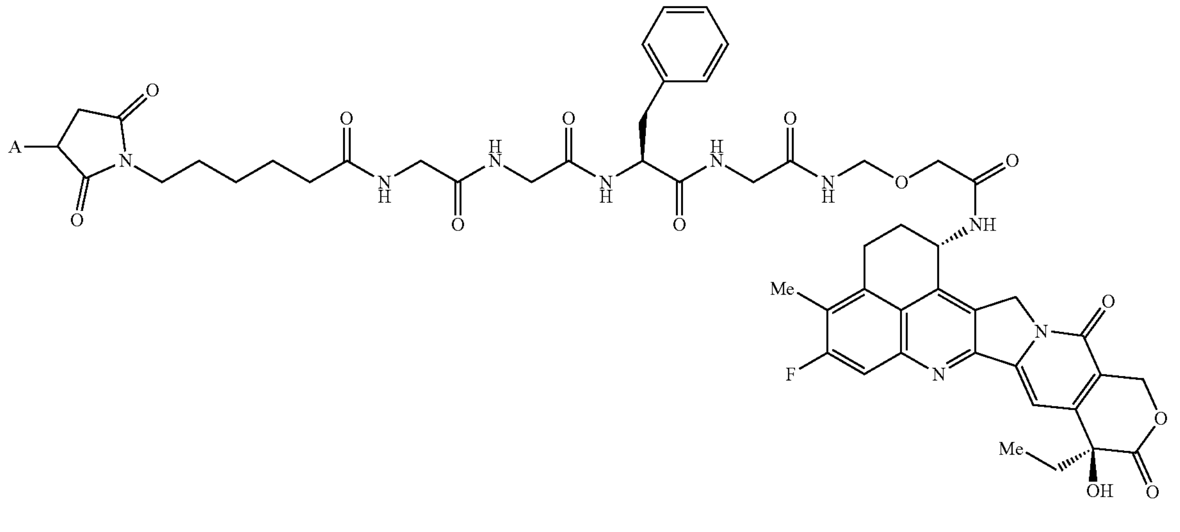

wherein A represents the connecting position to an antibody, is conjugated to an anti-HER2 antibody via a thioether bond.

In the present disclosure, the partial structure consisting of a linker and a drug in the antibody-drug conjugate is referred to as a “drug-linker”. The drug-linker is connected to a thiol group (in other words, the sulfur atom of a cysteine residue) formed at an interchain disulfide bond site (two sites between heavy chains, and two sites between a heavy chain and a light chain) in the antibody.

The drug-linker of the present disclosure includes exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione, (also expressed as chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione)), which is a topoisomerase I inhibitor, as a component. Exatecan is a camptothecin derivative having an antitumor effect, represented by the following formula:

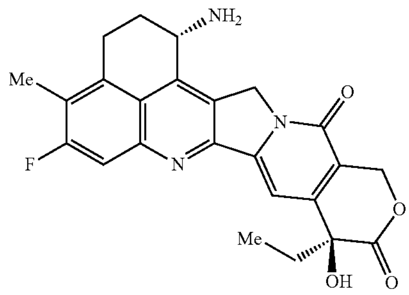 [SMILES: CC[C@@]1(O)C(=O)OCc2c1cc1n(c2=O)Cc2c-1nc1cc(F)c(C)c3c1c2[C@@H](N)CC3]

The anti-HER2 antibody-drug conjugate used in the present disclosure can be also represented by the following formula:

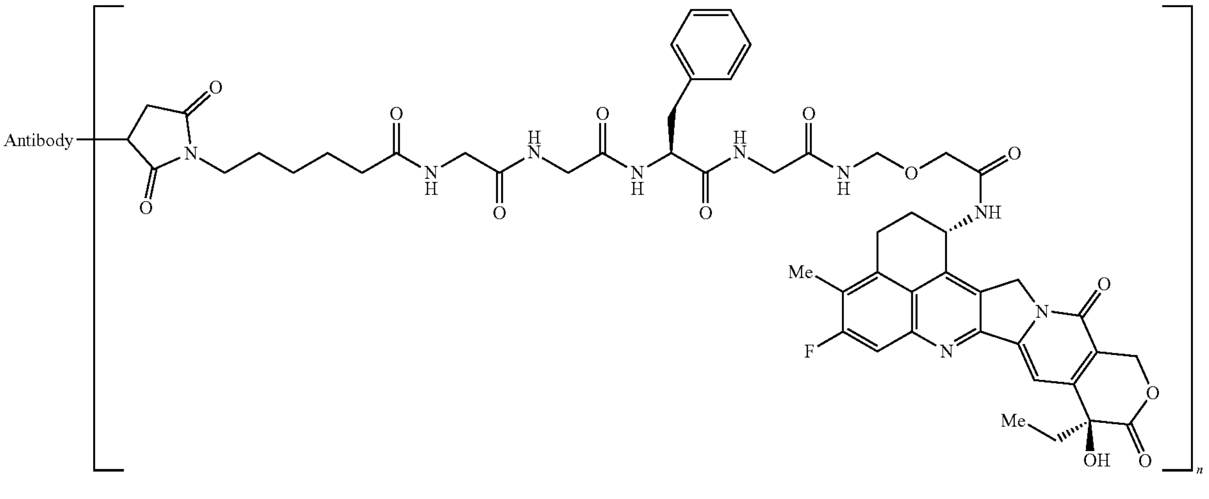

Here, the drug-linker is conjugated to an anti-HER2 antibody (‘Antibody-’) via a thioether bond. The meaning of n is the same as that of what is called the average number of conjugated drug molecules (DAR; Drug-to-Antibody Ratio), and indicates the average number of units of the drug-linker conjugated per antibody molecule.

After migrating into cancer cells, the anti-HER2 antibody-drug conjugate used in the present disclosure is cleaved at the linker portion to release a compound represented by the following formula:

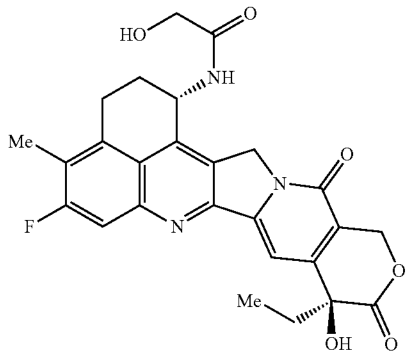 [SMILES: CC[C@@]1(O)C(=O)OCc2c1cc1n(c2=O)Cc2c-1nc1cc(F)c(C)c3c1c2[C@@H](NC(=O)CO)CC3]

This compound is inferred to be the original source of the antitumor activity of the antibody-drug conjugate used in the present disclosure, and has been confirmed to have a topoisomerase I inhibitory effect (Ogitani Y. et al., Clinical Cancer Research, 2016, Oct. 15; 22(20):5097-5108, Epub 2016 Mar. 29).

The anti-HER2 antibody-drug conjugate used in the present disclosure is known to have a bystander effect (Ogitani Y. et al., Cancer Science (2016) 107, 1039-1046). The bystander effect is exerted through a process whereby the antibody-drug conjugate used in the present disclosure is internalized in cancer cells expressing the target and the compound released then exerts an antitumor effect also on cancer cells which are present therearound and not expressing the target. This bystander effect is exerted as an excellent antitumor effect even when the anti-HER2 antibody-drug conjugate is used in combination with a CDK9 inhibitor according to the present disclosure.

2. Antibody in Antibody-Drug Conjugate

The anti-HER2 antibody in the antibody-drug conjugate used in the present disclosure may be derived from any species, and is preferably an anti-HER2 antibody derived from a human, a rat, a mouse, or a rabbit. In cases when the antibody is derived from species other than human species, it is preferably chimerized or humanized using a well known technique. The anti-HER2 antibody may be a polyclonal antibody or a monoclonal antibody and is preferably a monoclonal antibody.

The antibody in the antibody-drug conjugate used in the present disclosure is an anti-HER2 antibody preferably having a characteristic of being capable of targeting cancer cells, and is preferably an antibody possessing, for example, a property of recognizing a cancer cell, a property of binding to a cancer cell, a property of internalizing in a cancer cell, and/or cytocidal activity against cancer cells.

The binding activity of the anti-HER2 antibody against cancer cells can be confirmed using flow cytometry. The internalization of the antibody into cancer cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the anti-HER2 antibody can be confirmed in vitro by determining inhibitory activity against cell growth. For example, a cancer cell line overexpressing HER2 as a target protein for the antibody is cultured, and the antibody is added at varying concentrations into the culture system to determine inhibitory activity against focus formation, colony formation, and spheroid growth. The antitumor activity can be confirmed in vivo, for example, by administering the antibody to a nude mouse with a transplanted cancer cell line highly expressing the target protein, and determining change in the cancer cell.

Since the compound conjugated in the anti-HER2 antibody-drug conjugate exerts an antitumor effect, it is preferred but not essential that the anti-HER2 antibody itself should have an antitumor effect. For the purpose of specifically and selectively exerting the cytotoxic activity of the antitumor compound against cancer cells, it is important and also preferred that the anti-HER2 antibody should have the property of internalizing to migrate into cancer cells.

The anti-HER2 antibody in the antibody-drug conjugate used in the present disclosure can be obtained by a procedure known in the art. For example, the antibody of the present disclosure can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The anti-HER2 antibody in the antibody-drug conjugate used the present disclosure is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), and an antibody obtained by grafting a part of the amino acid residues of the framework of a heterologous antibody as well as the CDR sequence of the heterologous antibody to a human antibody by a CDR-grafting method (WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002)43 (7), p. 2301-2308; Carmen, S. et. al., Briefings in Functional Genomics and Proteomics (2002), 1(2), p. 189-203; Siriwardena, D. et. al., Ophthalmology (2002) 109(3), p. 427-431, etc.) can be exemplified.

In the present disclosure, modified variants of the anti-HER2 antibody in the antibody-drug conjugate used in the present disclosure are also included. The modified variant refers to a variant obtained by subjecting the antibody according to the present disclosure to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present disclosure, for example, an enzyme-labeled antibody, a fluorescence-labeled antibody, and an affinity-labeled antibody are also included in the meaning of the modified variant. Such a modified variant of the antibody according to the present disclosure is useful for improving the stability and blood retention of the antibody, reducing the antigenicity thereof, detecting or isolating an antibody or an antigen, and so on.

Further, by regulating the modification of a glycan which is linked to the antibody according to the present disclosure (glycosylation, defucosylation, etc.), it is possible to enhance antibody-dependent cellular cytotoxic activity. As the technique for regulating the modification of a glycan of antibodies, those disclosed in WO99/54342, WO00/61739, WO02/31140, WO2007/133855, WO2013/120066, etc. are known. However, the technique is not limited thereto. In the anti-HER2 antibody according to the present disclosure, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of complement, antibody-dependent cellular cytotoxicity, etc.) of the antibody. Therefore, in the anti-HER2 antibody according to the present disclosure, antibodies subjected to such modification and functional fragments of the antibody are also included, and deletion variants in which one or two amino acids have been deleted at the carboxyl terminus of the heavy chain, variants obtained by amidation of deletion variants (for example, a heavy chain in which the carboxyl terminal proline residue has been amidated), and the like are also included. The type of deletion variant having a deletion at the carboxyl terminus of the heavy chain of the anti-HER2 antibody according to the present disclosure is not limited to the above variants as long as the antigen-binding affinity and the effector function are conserved. The two heavy chains constituting the antibody according to the present disclosure may be of one type selected from the group consisting of a full-length heavy chain and the above-described deletion variant, or may be of two types in combination selected therefrom. The ratio of the amount of each deletion variant can be affected by the type of cultured mammalian cells which produce the anti-HER2 antibody according to the present disclosure and the culture conditions; however, an antibody in which one amino acid residue at the carboxyl terminus has been deleted in both of the two heavy chains in the antibody according to the present disclosure can be exemplified as preferred.

As isotypes of the anti-HER2 antibody according to the present disclosure, for example, IgG (IgG1, IgG2, IgG3, IgG4) can be exemplified, and IgG1 or IgG2 can be exemplified as preferred.

In the present disclosure, the term "anti-HER2 antibody" refers to an antibody which specifically binds to HER2 (Human Epidermal Growth Factor Receptor Type 2; ErbB-2), and preferably has an activity of internalizing in HER2-expressing cells by binding to HER2.

Examples of the anti-HER2 antibody include trastuzumab (U.S. Pat. No. 5,821,337) and pertuzumab (WO01/00245), and trastuzumab can be exemplified as preferred.

3. Production of Antibody-Drug Conjugate

A drug-linker intermediate for use in production of the anti-HER2 antibody-drug conjugate according to the present disclosure is represented by the following formula:

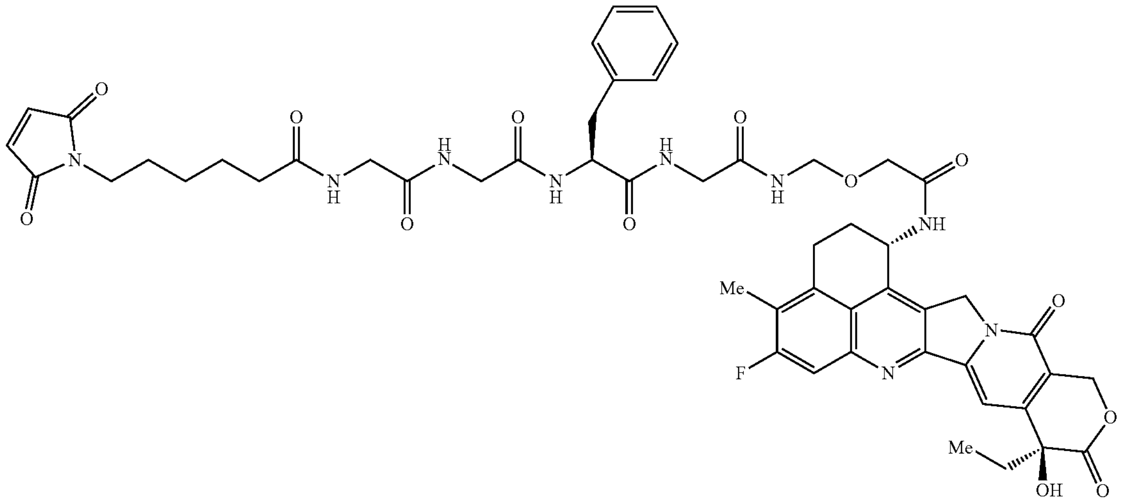 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)C=CC1=O)CC3]

The drug-linker intermediate can be expressed as the chemical name N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, and can be produced with reference to descriptions in WO2014/057687, WO2015/098099, WO2015/115091, WO2015/155998, WO2019/044947 and so on.

The anti-HER2 antibody-drug conjugate used in the present disclosure can be produced by reacting the above-described drug-linker intermediate and an anti-HER2 antibody having a thiol group (also referred to as a sulfhydryl group).

The anti-HER2 antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl) phosphine hydrochloride (TCEP) per interchain disulfide within the antibody and reacting with the antibody in a buffer solution containing a chelating agent such as ethylenediamine tetraacetic acid (EDTA), an anti-HER2 antibody having a sulfhydryl group with partially or completely reduced interchain disulfides within the antibody can be obtained.

Further, by using 2 to 20 molar equivalents of the drug-linker intermediate per anti-HER2 antibody having a sulfhydryl group, an anti-HER2 antibody-drug conjugate in which 2 to 8 drug molecules are conjugated per antibody molecule can be produced.

The average number of conjugated drug molecules per anti-HER2 antibody molecule of the antibody-drug conjugate produced can be determined, for example, by a method of calculation based on measurement of UV absorbance for the antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the anti-HER2 antibody and the drug-linker intermediate and calculation of the average number of conjugated drug molecules per antibody molecule of the antibody-drug conjugate can be performed with reference to descriptions in WO2014/057687, WO2015/098099, WO2015/115091, WO2015/155998, WO2017/002776, WO2018/212136, and so on.

In the present disclosure, the term "anti-HER2 antibody-drug conjugate" refers to an antibody-drug conjugate such that the antibody in the antibody-drug conjugate according to the present disclosure is an anti-HER2 antibody.

The anti-HER2 antibody is preferably an antibody comprising a heavy chain comprising CDRH1 consisting of an amino acid sequence consisting of amino acid residues 26 to 33 of SEQ ID NO: 1, CDRH2 consisting of an amino acid sequence consisting of amino acid residues 51 to 58 of SEQ ID NO: 1 and CDRH3 consisting of an amino acid sequence consisting of amino acid residues 97 to 109 of SEQ ID NO: 1, and a light chain comprising CDRL1 consisting of an amino acid sequence consisting of amino acid residues 27 to 32 of SEQ ID NO: 2, CDRL2 consisting of an amino acid sequence consisting of amino acid residues 50 to 52 of SEQ ID NO: 2 and CDRL3 consisting of an amino acid sequence consisting of amino acid residues 89 to 97 of SEQ ID NO: 2, and more preferably an antibody comprising a heavy chain comprising a heavy chain variable region consisting of an amino acid sequence consisting of amino acid residues 1 to 120 of SEQ ID NO: 1 and a light chain comprising a light chain variable region consisting of an amino acid sequence consisting of amino acid residues 1 to 107 of SEQ ID NO: 2, and even more preferably an antibody comprising a heavy chain consisting of an amino acid sequence represented by SEQ ID NO: 1 and a light chain consisting of the amino acid sequence represented by SEQ ID NO: 2, or an antibody comprising a heavy chain consisting of amino acid residues 1 to 449 of SEQ ID NO: 1 and a light chain consisting of an amino acid sequence consisting of all amino acid residues 1 to 214 of SEQ ID NO: 2.

The average number of units of the drug-linker conjugated per antibody molecule in the anti-HER2 antibody-drug conjugate is preferably 2 to 8, more preferably 3 to 8, even more preferably 7 to 8, even more preferably 7.5 to 8, and even more preferably about 8.

The anti-HER2 antibody-drug conjugate used in the present disclosure can be produced with reference to descriptions in WO2015/115091 and so on.

In preferred embodiments, the anti-HER2 antibody-drug conjugate is trastuzumab deruxtecan (DS-8201).

4. CDK9 Inhibitor

In the present disclosure, the term "CDK9 inhibitor" refers to an agent that inhibits cyclin dependent kinase 9 (CDK9). The CDK9 inhibitor in the present disclosure may selectively inhibit the kinase CDK9, or may non-selectively inhibit CDK9 and inhibit also kinase(s) other than CDK9. The CDK9 inhibitor in the present disclosure is not particularly limited as long as it is an agent that has the described characteristics, and preferred examples thereof can include those disclosed in WO2017/001354.

Examples of CDK9 inhibitors which may be used according to the present disclosure are selective inhibitors of CDK9 including AZD4573, BAY-1251152, and BAY-1143572, and non-selective inhibitors of CDK9 include CYC065, alvocidib, AT7519, voruciclib, roniciclib, and dinaciclib.

Preferably, the CDK9 inhibitor in the present disclosure inhibits CDK9 selectively.

According to preferred embodiments of the CDK9 inhibitor used in the present disclosure, the CDK9 inhibitor is a compound represented by the following formula (I):

(I)

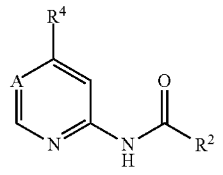

wherein:

A is $C(R^5)$ or N;

$R^5$ is H, $C_{1-3}$ alkyl, CN or halogen;

$R^2$ is 3-7 membered heterocycloalkyl or 3-7 membered cycloalkyl; optionally substituted with one to three substituents independently selected from the group consisting of $R^{10}$, $OR^{10}$, $SR^{10}$, $S(O) R^{10}$, $S(O)_2R^{10}$, $C(O) R^{10}$, $C(O)OR^{10}$, $OC(O)R^{10}$, $OC(O)OR^{10}$, $NH_2$, $NHR^{10}$, $N(R^{10})_2$, $NHC(O)H$, $NHC(O)R^{10}$, $NR^{10}C(O)H$, $NR^{10}C(O)R^{10}$, $NHS(O)_2R^{10}$, $NR^{10}S(O)_2R^{10}$, $NHC(O)OR^{10}$, $NR^{10}C(O)OR^{10}$, $NHC(O)NH_2$, $NHC(O)NHR^{10}$, $NHC(O)N(R^{10})_2$, $NR^{10}C(O)NH_2$, $NR^{10}C(O)NHR^{10}$, $NR^{10}C(O)N(R^{10})_2$, $C(O)NH_2$, $C(O)NHR^{10}$, $C(O)N(R^{10})_2$, $C(O)NHOH$, $C(O)NHOR^{10}$, $C(O) NHS(O)_2R^{10}$, $C(O) NR^{10}S(O)_2R^{10}$, $S(O)_2NH_2$, $S(O)_2NHR^{10}$, $S(O)_2N(R^{10})_2$, $S(O)_2NHC(O) OR^{10}$, $S(O)_2NR^{10}C(O) OR^{10}$, C(O) H, C(O)OH, OH, CN, $NO_2$, F, Cl, Br and I; wherein one or more ring $CH_2$ groups can optionally be replaced by a corresponding number of —C(O) groups, one or more ring sulfur or nitrogen atoms may be optionally oxidized to form S-oxides or N-oxides;

$R^{10}$, at each occurrence, is independently selected from the group consisting of a 3 to 6 membered cycloalkyl or heterocycloalkyl group, $C_{1-6}$ alkyl, —O—$C_{1-6}$ alkyl, $C_{1-6}$ alkyl-O—$C_{1-6}$ alkyl, $NH_2$, $C(O)NH_2$, C(O)H, C(O)OH, OH, CN, $NO_2$, F, Cl, Br and I; wherein two $R^{10}$ groups together with the atoms to which they are attached may form a 3 to 6 membered cycloalkyl or heterocycloalkyl group; and each aforementioned $R^{10}$ alkyl, cycloalkyl and heterocycloalkyl group may be further substituted with one or two substituents independently selected from CN, OH, halogen, $C_{1-3}$ alkyl, —O—$C_{1-3}$ alkyl, $NH_2$, NH—$C_{1-3}$ alkyl, and NHC(O)—$C_{1-3}$ alkyl;

$R^4$ is

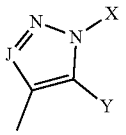
or
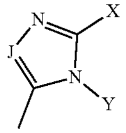

wherein X and Y together with the atoms to which they are attached, form a 5 to 7 membered heterocycloalkyl ring which, in addition to the bridge nitrogen, may contain one or two heteroatoms selected from N, O, and S which ring may be saturated or partially saturated; wherein one or two ring $CH_2$ groups can optionally be replaced by a corresponding number of —C(O) groups, one or more ring sulfur or nitrogen atoms which may be optionally oxidized to form S-oxides or N-oxides and wherein the ring may be substituted on a ring carbon by one or two $R^{10}$ substituents or on a ring nitrogen by an $R^{12}$ substituent;

J is N or $CR^{11}$;

$R^{11}$ is H, $C_{1-3}$ alkyl; and $R^{12}$ is at each occurrence independently selected from the group consisting of a 3 to 6 membered cycloalkyl or heterocycloalkyl group, $C_{1-6}$ alkyl, $C_{1-6}$ alkyl-O—$C_{1-6}$ alkyl, $C(O)NH_2$, O(O)H; wherein each $R^{12}$ alkyl, cycloalkyl and heterocycloalkyl group may be further substituted with one or two substituents independently selected from CN, OH, and halogen, $C_{1-3}$ alkyl, $NH_2$, and NH— $C_{1-3}$ alkyl, NHC(O)—$C_{1-3}$ alkyl, or pharmaceutical acceptable salts thereof.

Additional embodiments of the CDK9 inhibitor are compounds of formula (I), and pharmaceutically acceptable salts thereof, in which substituents are defined as follows. Such specific substituents may be used, where appropriate, with any of the definitions, claims or embodiments defined herein.

A

In one embodiment, A is $C(R^5)$.

$R^5$

In one embodiment $R^5$ is halogen.

In another embodiment $R^5$ is chloro.

In another embodiment $R^5$ is fluoro.

In another embodiment $R^5$ is cyano.

$R^2$

In one embodiment $R^2$ is 3-7 membered cycloalkyl.

In another embodiment $R^2$ is 3-7 membered cycloalkyl substituted with $NHCOR^{10}$ or $R^{10}$.

In another embodiment $R^2$ is cyclohexyl substituted with $NHCOR^{10}$.

In another embodiment $R^2$ is cyclopropyl substituted with $R^{10}$.

In another embodiment $R^2$ is 3-7 membered heterocycloalkyl.

In another embodiment $R^2$ is 3-7 membered heterocycloalkyl substituted with $NHCOR^{10}$.

In another embodiment $R^2$ is piperidinyl.

In another embodiment $R^2$ is cyclobutyl.

In another embodiment $R^2$ is cyclobutyl substituted with $R^{10}$.

$R^4$

In one embodiment $R^4$ is

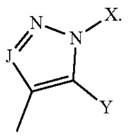

In another embodiment $R^4$ is

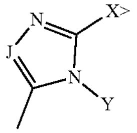

J

In one embodiment J is $C(R^{11})$ and $R^{11}$ is H.

X and Y

In one embodiment X and Y together with the atoms to which they are attached form a 6 membered heterocycloalkyl ring.

In another embodiment X and Y together with the atoms to which they are attached form a 6 membered heterocycloalkyl ring containing an additional heteroatom which is oxygen.

In another embodiment X and Y together with the atoms to which they are attached form a 6 membered heterocycloalkyl ring containing an additional heteroatom which is nitrogen.

In another embodiment X and Y together with the atoms to which they are attached form a 6 membered heterocycloalkyl ring in which one $CH_2$ is substituted with two methyl groups.

In another embodiment X and Y together with the atoms to which they are attached form a 5 membered heterocycloalkyl ring.

In another embodiment X and Y together with the atoms to which they are attached form a 5 membered heterocycloalkyl ring in which one $CH_2$ is substituted with two methyl groups.

In another embodiment X and Y together with the atoms to which they are attached form a 7 membered heterocycloalkyl ring.

In another embodiment X and Y together with the atoms to which they are attached form a 7 membered heterocycloalkyl ring in which one $CH_2$ is substituted with two methyl groups.

In one embodiment

A is $C(R^5)$;

$R^2$ is 3-7 membered cycloalkyl;

$R^4$ is

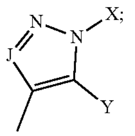

and

X and Y together with the atoms to which they are attached form a 6 membered heterocycloalkyl ring.

In another embodiment

A is $C(R^5)$;

$R^5$ is halogen;

$R^2$ is 3-7 membered cycloalkyl;

$R^4$ is

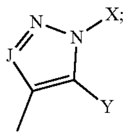

and

X and Y together with the atoms to which they are attached form a 6 membered heterocycloalkyl ring.

In another embodiment

A is $C(R^5)$;

$R^5$ is chloro;

$R^2$ is 3-7 membered cycloalkyl;

$R^4$ is

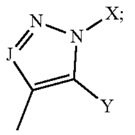

and

X and Y together with the atoms to which they are attached form a 6 membered heterocycloalkyl ring.

In another embodiment

A is $C(R^5)$;

$R^5$ is chloro;

$R^2$ is cyclohexyl;

$R^4$ is

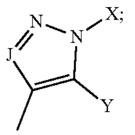

and

X and Y together with the atoms to which they are attached form a 6 membered heterocycloalkyl ring.

In another embodiment

A is $C(R^5)$;

$R^5$ is chloro;

$R^2$ is cyclohexyl substituted with $NHC(O)R^{10}$;

$R^4$ is

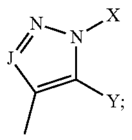

and

X and Y together with the atoms to which they are attached form a 6 membered heterocycloalkyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

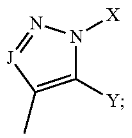

J is $C(R^{11})$ and $R^{11}$ is H; and

X and Y together with the atoms to which they are attached form a 6 membered heterocycloalkyl ring.

In another embodiment

A is $C(R^5)$;

$R^2$ is 3-7 membered cycloalkyl;

$R^4$ is

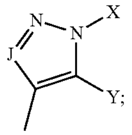

and

X and Y together with the atoms to which they are attached form a 5 membered heterocycloalkyl ring.

In another embodiment

A is $C(R^5)$;

$R^5$ is halogen;

$R^2$ is cyclohexyl;

$R^4$ is

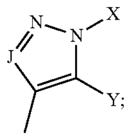

and

X and Y together with the atoms to which they are attached form a 5 membered heterocycloalkyl ring.

In another embodiment

A is $C(R^5)$;

$R^5$ is chloro;

$R^2$ is cyclohexyl;

$R^4$ is

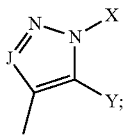

and

X and Y together with the atoms to which they are attached form a 5 membered heterocycloalkyl ring.

In another embodiment

A is $C(R^5)$;

$R^5$ is chloro;

$R^2$ is cyclohexyl substituted with $NHC(O)R^{10}$;

$R^4$ is

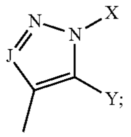

and

X and Y together with the atoms to which they are attached form a 5 membered heterocycloalkyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

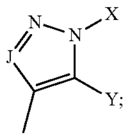

J is $C(R^{11})$ and $R^{11}$ is H; and

X and Y together with the atoms to which they are attached form a 5 membered heterocycloalkyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

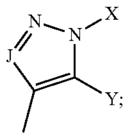

J is $C(R^{11})$ and $R^{11}$ is H; and

X and Y together with the atoms to which they are attached form a piperidinyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

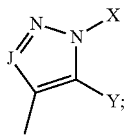

J is $C(R^{11})$ and $R^{11}$ is H; and

X and Y together with the atoms to which they are attached form a piperidinyl ring wherein one ring carbon may be substituted by one or two $R^{10}$ substituents.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

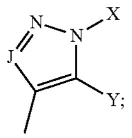

J is $C(R^{11})$ and $R^{11}$ is H; and

X and Y together with the atoms to which they are attached form a piperazinyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

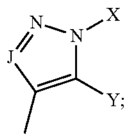

J is $C(R^{11})$ and $R^{11}$ is H; and

X and Y together with the atoms to which they are attached form a morpholinyl ring.

In another embodiment

A is $C(R^5)$;

$R^5$ is chloro;

$R^2$ is cyclohexyl substituted with $NHC(O)R^{10}$;

$R^{10}$ is $C_{1-6}$ alkyl;

$R^4$ is

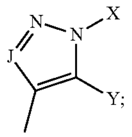

J is $C(R^{11})$ and $R^{11}$ is H; and

X and Y together with the atoms to which they are attached form a pyrrolidinyl wherein one $CH_2$ is substituted with two methyl groups.

In another embodiment

A is C($R^5$);

$R^2$ is 3-7 membered cycloalkyl;

$R^4$ is

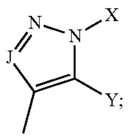

and

X and Y together with the atoms to which they are attached form a 7 membered heterocycloalkyl ring.

In one embodiment

A is C($R^5$);

$R^5$ is halogen;

$R^2$ is 3-7 membered cycloalkyl;

$R^4$ is

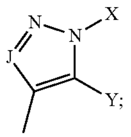

and

X and Y together with the atoms to which they are attached form a 7 membered heterocycloalkyl ring.

In another embodiment

A is C($R^5$);

$R^5$ is chloro;

$R^2$ is 3-7 membered cycloalkyl;

$R^4$ is

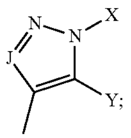

and

X and Y together with the atoms to which they are attached form a 7 membered heterocycloalkyl ring.

In another embodiment

A is C($R^5$);

$R^5$ is chloro;

$R^2$ is cyclohexyl;

$R^4$ is

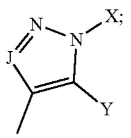

and

X and Y together with the atoms to which they are attached form a 7 membered heterocycloalkyl ring.

In another embodiment

A is C($R^5$);

$R^5$ is chloro;

$R^2$ is cyclohexyl substituted with NHC(O)$R^{10}$;

$R^4$ is

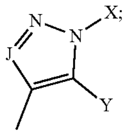

and

X and Y together with the atoms to which they are attached form a 7 membered heterocycloalkyl ring.

In another embodiment

A is C($R^5$);

$R^5$ is chloro;

$R^2$ is cyclohexyl substituted with NHC(O)$R^{10}$;

$R^{10}$ is $C_{1-6}$ alkyl;

$R^4$ is

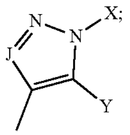

J is C($R^{11}$) and $R^{11}$ is H; and

X and Y together with the atoms to which they are attached form a 7 membered heterocycloalkyl ring.

In other embodiments, the CDK9 inhibitor used in the disclosure is a compound selected from:

(R)—N-(5-chloro-4-(5,6,7,8-tetrahydroimidazo[1,2-a]pyridin-3-yl)pyridin-2-yl)piperidine-3-carboxamide;

(1S,3R)-3-acetamido-N-(5-chloro-4-(4,5,6,7-tetrahydropyrazolo[1,5-a]pyridin-3-yl)pyridin-2-yl)cyclohexanecarboxamide;

(1S,3R)-3-acetamido-N-(4-(4,5,6,7-tetrahydropyrazolo[1,5-a]pyridin-3-yl)pyridin-2-yl)cyclohexanecarboxamide;

Cis-N-(5-chloro-4-(4,5,6,7-tetrahydropyrazolo[1,5-a]pyridin-3-yl)pyridin-2-yl)-3-hydroxycyclobutanecarboxamide;

(R)—N-(5-chloro-4-(4,5,6,7-tetrahydropyrazolo[1,5-a]pyridin-3-yl)pyridin-2-yl)piperidine-3-carboxamide; cis-3-hydroxy-N-(4-(4,5,6,7-tetrahydropyrazolo[1,5-a]pyridin-3-yl)pyridin-2-yl)cyclobutanecarboxamide;

(1S,3R)-3-acetamido-N-(5-chloro-4-(5,6,7,8-tetrahydroimidazo[1,2-a]pyridin-3-yl)pyridin-2-yl)cyclohexanecarboxamide;

(1S,3R)-3-acetamido-N-(5-chloro-4-(6,7-dihydro-5H-pyrazolo[5,1-b][1,3]oxazin-3-yl)pyridin yl)cyclohexanecarboxamide; (1R,3S)-3-acetamido-N-(5-chloro-4-(4,5,6,7-tetrahydropyrazolo[1,5-a]pyridin yl)pyridin-2-yl) cyclohexanecarboxamide;

(1S,3R)-3-acetamido-N-(5-chloro-4-(5,6-dihydro-4H-pyrrolo[1,2-b]pyrazol-3-yl)pyridin yl)cyclohexanecarboxamide;

(1S,3R)-3-acetamido-N-(5-chloro-4-(6,7-dihydro-4H-pyrazolo[5,1-c][1,4]oxazin-3-yl)pyridin-2-yl)cyclohexanecarboxamide;

(1S,3R)-3-acetamido-N-(5-chloro-4-(6,7-dihydro-5H-pyrrolo[1,2-a]imidazol-3-yl)pyridin-2-yl)cyclohexanecarboxamide;

(1S,3R)-3-acetamido-N-(5-chloro-4-(5-methyl-4,5,6,7-tetrahydropyrazolo[1,5-a]pyrazin-3-yl)pyridin-2-yl)cyclohexanecarboxamide;

(1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

(1S,3R)-3-acetamido-N-(5-chloro-4-(4,5,6,7-tetrahydropyrazolo[1,5-a]pyrimidin-3-yl)pyridin-2-yl)cyclohexanecarboxamide;

(1S,3R)-3-acetamido-N-(4-(5,5-dimethyl-5,6-dihydro-4H-pyrrolo[1,2-b]pyrazol-3-yl)pyridin-2-yl)cyclohexanecarboxamide;

(1S,3R)—N-(4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide;

N-((1R,3S)-3-((4-(5,5-dimethyl-5,6-dihydro-4H-pyrrolo[1,2-b]pyrazol-3-yl)pyridin yl)carbamoyl)cyclohexyl)oxetane-3-carboxamide;

N-((1R,3S)-3-((5-chloro-4-(5,5-dimethyl-5,6-dihydro-4H-pyrrolo[1,2-b]pyrazol-3-yl)pyridin yl)carbamoyl)cyclohexyl)oxetane-3-carboxamide;

(1S,3R)—N-(5-chloro-4-(5,5-dimethyl-5,6-dihydro-4H-pyrrolo[1,2-b]pyrazol-3-yl)pyridin-2-yl)-3-((S)-2-hydroxypropanamido)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(1-hydroxycyclopropanecarboxamido)cyclohexanecarboxamide;

(1S,3R)-3-acetamido-N-(5-chloro-4-(6,6-dimethyl-6,7-dihydro-5H-pyrrolo[1,2-a]imidazol-3-yl)pyridin-2-yl)cyclohexanecarboxamide;

(R)—N-((1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide;

(S)—N—(1R,3S)-3-((5-chloro-4-(5,5-dimethyl-5,6-dihydro-4H-pyrrolo[1,2-b]pyrazol-3-yl)pyridin-2-yl)carbamoyl)cyclohexyl)tetrahydrofuran-3-carboxamide;

(1S,3R)-3-acetamido-N-(4-(5,5-dimethyl-5,6-dihydro-4H-pyrrolo[1,2-b]pyrazol-3-yl)-5-fluoropyridin-2-yl)cyclohexanecarboxamide;

cis-N-(4-(5,5-dimethyl-5,6-dihydro-4H-pyrrolo[1,2-b]pyrazol-3-yl)pyridin-2-yl) hydroxycyclobutanecarboxamide;

cis-N-(5-chloro-4-(5,5-dimethyl-5,6-dihydro-4H-pyrrolo[1,2-b]pyrazol-3-yl)pyridin-2-yl) hydroxycyclobutanecarboxamide;

(1S,3R)-3-acetamido-N-(6-(4,5,6,7-tetrahydropyrazolo[1,5-a]pyridin-3-yl)pyrimidin-4-yl)cyclohexanecarboxamide;

trans-3-hydroxy-N-(6-(4,5,6,7-tetrahydropyrazolo[1,5-a]pyridin-3-yl)pyrimidin-4-yl)cyclobutanecarboxamide;

(1S,3R)-3-acetamido-N-(6-(5,5-dimethyl-5,6-dihydro-4H-pyrrolo[1,2-b]pyrazol-3-yl)pyrimidin-4-yl)cyclohexanecarboxamide;

(1S,3R)—N-(5-chloro-4-(4,5,6,7-tetrahydropyrazolo[1,5-a]pyridin-3-yl)pyridin-2-yl)-3-(2-cyanoacetamido)cyclohexanecarboxamide;

tert-butyl ((1R,3S)-3-((5-chloro-4-(4,5,6,7-tetrahydropyrazolo[1,5-a]pyridin-3-yl)pyridin-2-yl)carbamoyl)cyclohexyl)carbamate;

(1S,3R)-3-amino-N-(5-chloro-4-(4,5,6,7-tetrahydropyrazolo[1,5-a]pyridin-3-yl)pyridin-2-yl)cyclohexanecarboxamide;

(1S,3R)—N-(5-chloro-4-(4,5,6,7-tetrahydropyrazolo[1,5-a]pyridin-3-yl)pyridin-2-yl)-3-(1-hydroxycyclopropanecarboxamido)cyclohexanecarboxamide;

(R)—N-((1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide;

N-((1R,3S)-3-((5-chloro-4-(4,5,6,7-tetrahydropyrazolo[1,5-a]pyridin-3-yl)pyridin yl)carbamoyl)cyclohexyl)-3-methyloxetane-3-carboxamide;

(S)—N-((1R,3S)-3-((5-chloro-4-(4,5,6,7-tetrahydropyrazolo[1,5-a]pyridin-3-yl)pyridin yl)carbamoyl)cyclohexyl)tetrahydrofuran-2-carboxamide;

(R)—N-((1R,3S)-3-((5-chloro-4-(4,5,6,7-tetrahydropyrazolo[1,5-a]pyridin-3-yl)pyridin yl)carbamoyl)cyclohexyl)tetrahydrofuran-2-carboxamide;

(1S,3R)—N-(5-chloro-4-(4,5,6,7-tetrahydropyrazolo[1,5-a]pyridin-3-yl)pyridin-2-yl)-3-((S)-2-hydroxypropanamido)cyclohexanecarboxamide;

(S)—N—(1R,3S)-3-((5-chloro-4-(4,5,6,7-tetrahydropyrazolo[1,5-a]pyridin-3-yl)pyridin-2-yl)carbamoyl)cyclohexyl)tetrahydrofuran-3-carboxamide;

(1S,3R)-3-acetamido-N-(5-cyano-4-(5,5-dimethyl-5,6-dihydro-4H-pyrrolo[1,2-b]pyrazol-3-yl)pyridin-2-yl)cyclohexanecarboxamide;

Isomer 1 of (1S,3R)-3-acetamido-N-(5-chloro-4-(5-methyl-5,6-dihydro-4H-pyrrolo[1,2-b]pyrazol-3-yl)pyridin-2-yl) cyclohexanecarboxamide;

Isomer 2 of (1S,3R)-3-acetamido-N-(5-chloro-4-(5-methyl-5,6-dihydro-4H-pyrrolo[1,2-b]pyrazol-3-yl)pyridin-2-yl) cyclohexanecarboxamide;

(1R,3S)-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

(1S,3R)-3-acetamido-N-(4-(5,5-dimethyl-4,5,6,7-tetrahydropyrazolo[1,5-a]pyridin-3-yl)pyridin yl)cyclohexanecarboxamide;

(S)—N-((1R,3S)-3-((5-chloro-4-(5,5-dimethyl-5,6-dihydro-4H-pyrrolo[1,2-b]pyrazol-3-yl)pyridin yl)carbamoyl)cyclohexyl)tetrahydrofuran-2-carboxamide;

(R)—N-((1R,3S)-3-((5-chloro-4-(5,5-dimethyl-5,6-dihydro-4H-pyrrolo[1,2-b]pyrazol-3-yl)pyridin yl)carbamoyl)cyclohexyl)tetrahydrofuran-2-carboxamide;

(1S,3R)-3-acetamido-N-(4-(5,5-dimethyl-5,6-dihydro-4H-pyrrolo[1,2-b]pyrazol-3-yl)-5-methylpyridin-2-yl)cyclohexanecarboxamide;

(1S,3R)-3-acetamido-N-(5-chloro-4-(5,5-dimethyl-5,6-dihydro-4H-pyrrolo[1,2-b]pyrazol-3-yl)pyridin-2-yl)cyclopentanecarboxamide;

(1S,3R)-3-acetamido-N-(5-chloro-4-(4,5,6,7-tetrahydro-[1,2,3]triazolo[1,5-a]pyridin-3-yl)pyridin-2-yl)cyclohexanecarboxamide;

(1S,3R)-3-acetamido-N-(4-(6,6-dimethyl-6,7-dihydro-5H-pyrrolo[1,2-a]imidazol-3-yl)-5-fluoropyridin-2-yl)cyclohexanecarboxamide;

(1S,3R)-3-acetamido-N-(4-(5,5-dimethyl-4,5,6,7-tetrahydropyrazolo[1,5-a]pyridin-3-yl)-5-fluoropyridin-2-yl)cyclohexanecarboxamide;

(1S,3R)-3-amino-N-(4-(5,5-dimethyl-4,5,6,7-tetrahydropyrazolo[1,5-a]pyridin-3-yl)-5-fluoropyridin-2-yl)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(3-hydroxypropanamido)cyclohexanecarboxamide;

(1S,3R)—N-(5-chloro-4-(5,5-dimethyl-5,6-dihydro-4H-pyrrolo[1,2-b]pyrazol-3-yl)pyridin-2-yl)-3-(cis hydroxycyclobutanecarboxamido)cyclohexanecarboxamide (1S,3R)-3-amino-N-(4-(5,5-dimethyl-5,6-dihydro-4H-pyrrolo[1,2-b]pyrazol-3-yl)-5-fluoropyridin yl)cyclohexane-1-carboxamide;

(1S,3R)—N-(4-(5,5-dimethyl-5,6-dihydro-4H-pyrrolo[1,2-b]pyrazol-3-yl)-5-fluoropyridin-2-yl)-3-(1-hydroxycyclopropanecarboxamido)cyclohexanecarboxamide;

(1S,3R)—N-(5-chloro-4-(6,6-dimethyl-6,7-dihydro-5H-pyrrolo[1,2-a]imidazol-3-yl)pyridin-2-yl)-3-(1-hydroxy-cyclopropanecarboxamido)cyclohexanecarboxamide;

N-((1R,3S)-3-((5-chloro-4-(6,6-dimethyl-6,7-dihydro-5H-pyrrolo[1,2-a]imidazol-3-yl)pyridin-2-yl)carbamoyl)cyclohexyl)oxetane-3-carboxamide;

cis-N-(5-chloro-4-(6,6-dimethyl-6,7-dihydro-5H-pyrrolo[1,2-a]imidazol-3-yl)pyridin-2-yl)-3-hydroxycyclobutanecarboxamide;

Isomer 1 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

Isomer 2 of trans-3-acetamido-N-(5-chloro-4-(5,5-dimethyl-5,6-dihydro-4H-pyrrolo[1,2-b]pyrazol-3-yl)pyridin-2-yl)cyclohexanecarboxamide;

Isomer 1 of trans-3-acetamido-N-(5-chloro-4-(4,5,6,7-tetrahydropyrazolo[1,5-a]pyridin-3-yl)pyridin yl)cyclohexanecarboxamide;

Isomer 2 of trans-3-acetamido-N-(5-chloro-4-(4,5,6,7-tetrahydropyrazolo[1,5-a]pyridin-3-yl)pyridin yl)cyclohexanecarboxamide;

(1S,3R)-3-acetamido-N-(5-fluoro-4-(4,5,6,7-tetrahydropyrazolo[1,5-a]pyridin-3-yl)pyridin yl)cyclohexanecarboxamide;

Isomer 1 of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(5-methyl-4,5,6,7-tetrahydropyrazolo[1,5-a]pyridin-3-yl)pyridin-2-yl)cyclohexanecarboxamide;

(1S,3R)-3-acetamido-N-(5-chloro-4-(5,6,7,8-tetrahydro-4H-pyrazolo[1,5-a]azepin-3-yl)pyridin-2-yl)cyclohexanecarboxamide;

N-((1R,3S)-3-((5-chloro-4-(4,5,6,7-tetrahydropyrazolo[1,5-a]pyridin-3-yl)pyridin-2-yl)carbamoyl)cyclohexyl)oxetane-3-carboxamide;

Isomer 1 of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide;

Isomer 2 of (1S,3R)-3-acetamido-N-(5-chloro-4-(6-methyl-4,5,6,7-tetrahydropyrazolo[1,5-a]pyridin-3-yl)pyridin-2-yl)cyclohexanecarboxamide;

Isomer 1 of (1S,3R)-3-acetamido-N-(5-chloro-4-(6-methoxy-4,5,6,7-tetrahydropyrazolo[1,5-a]pyridin-3-yl)pyridin yl)cyclohexanecarboxamide;

Isomer 2 of (1S,3R)-3-acetamido-N-(5-chloro-4-(6-methoxy-4,5,6,7-tetrahydropyrazolo[1,5-a]pyridin-3-yl)pyridin yl)cyclohexanecarboxamide;

Isomer 1 of (1S,3R)-3-acetamido-N-(5-chloro-4-(5-methoxy-4,5,6,7-tetrahydropyrazolo[1,5-a]pyridin-3-yl)pyridin yl)cyclohexanecarboxamide;

Isomer 2 of (1S,3R)-3-acetamido-N-(5-chloro-4-(5-methoxy-4,5,6,7-tetrahydropyrazolo[1,5-a]pyridin-3-yl)pyridin-2-yl)cyclohexanecarboxamide;

(1S,3R)-3-acetamido-N-(5-fluoro-4-(5,6,7,8-tetrahydro-4H-pyrazolo[1,5-a]azepin-3-yl)pyridin-2-yl)cyclohexanecarboxamide;

(1S,3R)—N-(4-(5,5-dimethyl-5,6-dihydro-4H-pyrrolo[1,2-b]pyrazol-3-yl)-5-methylpyridin-2-yl)-3-(2-hydroxyacetamido)cyclohexanecarboxamide;

N-((1R,3S)-3-((4-(5,5-dimethyl-5,6-dihydro-4H-pyrrolo[1,2-b]pyrazol-3-yl)-5-methylpyridin-2-yl)carbamoyl)cyclohexyl)oxetane-3-carboxamide;

(1S,3R)-3-acetamido-N-(5-methyl-4-(4,5,6,7-tetrahydropyrazolo[1,5-a]pyridin-3-yl)pyridin-2-yl)cyclohexanecarboxamide;

(1S,3R)-3-acetamido-N-(5-chloro-4-(7-hydroxy-4,5,6,7-tetrahydropyrazolo[1,5-a]pyridin-3-yl)pyridin-2-yl)cyclohexanecarboxamide;

(1S,3R)-3-acetamido-N-(5-chloro-4-(5-(4-hydroxybutyl)-1H-pyrazol-4-yl)pyridin-2-yl)cyclohexanecarboxamide;

Isomer 1 of (1S,3R)-3-acetamido-N-(5-chloro-4-(4-hydroxy-5,5-dimethyl-5,6-dihydro-4H-pyrrolo[1,2-b]pyrazol yl)pyridin-2-yl)cyclohexanecarboxamide;

Isomer 2 of (1S,3R)-3-acetamido-N-(5-chloro-4-(4-hydroxy-5,5-dimethyl-5,6-dihydro-4H-pyrrolo[1,2-b]pyrazol yl)pyridin-2-yl)cyclohexanecarboxamide;

(1R,3S)-3-acetamido-N-(4-(5,5-dimethyl-5,6-dihydro-4H-pyrrolo[1,2-b]pyrazol-3-yl)-5-fluoropyridin-2-yl)cyclohexanecarboxamide;

(1S,3R)-3-acetamido-N-(5-chloro-4-(5-(3-hydroxy-2,2-dimethylpropyl)-1H-pyrazol-4-yl)pyridin-2-yl)cyclohexane-1-carboxamide;

(1S,3R)-3-acetamido-N-(5-chloro-4-(6-hydroxy-5,5-dimethyl-5,6-dihydro-4H-pyrrolo[1,2-b]pyrazol-3-yl)pyridin-2-yl)cyclohexane-1-carboxamide;

(1R,3R)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide; and (1S,3S)-3-acetamido-N-(4-(5,5-dimethyl-5,6-dihydro-4H-pyrrolo[1,2-b]pyrazol-3-yl)-5-fluoropyridin-2-yl)cyclohexane-1-carboxamide, and pharmaceutically acceptable salts thereof.

In a preferred embodiment the CDK9 inhibitor used in the disclosure is the compound AZD4573 represented by the following formula:

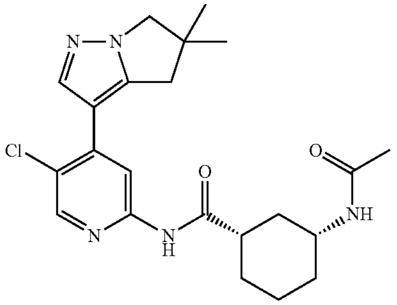 [SMILES: CC(=O)N[C@@H]1CCC[C@H](C(=O)Nc2cc(-c3cnn4c3CC(C)(C)C4)c(Cl)cn2)C1]

or a pharmaceutically acceptable salt thereof.

In a further preferred embodiment the CDK9 inhibitor used in the disclosure is the compound AZD4573 represented by the following formula:

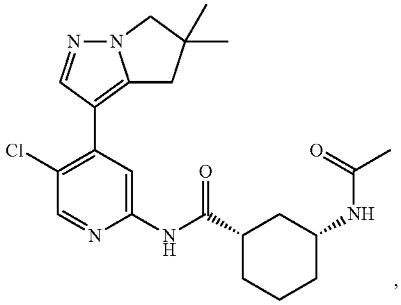 [SMILES: CC(=O)N[C@@H]1CCC[C@H](C(=O)Nc2cc(-c3cnn4c3CC(C)(C)C4)c(Cl)cn2)C1]

, in the free base form.

CDK9 inhibitors such as compounds of formula (I), including AZD4573, may be prepared by methods known in the art such as disclosed in WO2017/001354.

5. Combination of Antibody-Drug Conjugate and CDK9 Inhibitor

In a first combination embodiment of the disclosure, the anti-HER2 antibody-drug conjugate which is combined with the CDK9 inhibitor is an antibody-drug conjugate in which a drug-linker represented by the following formula:

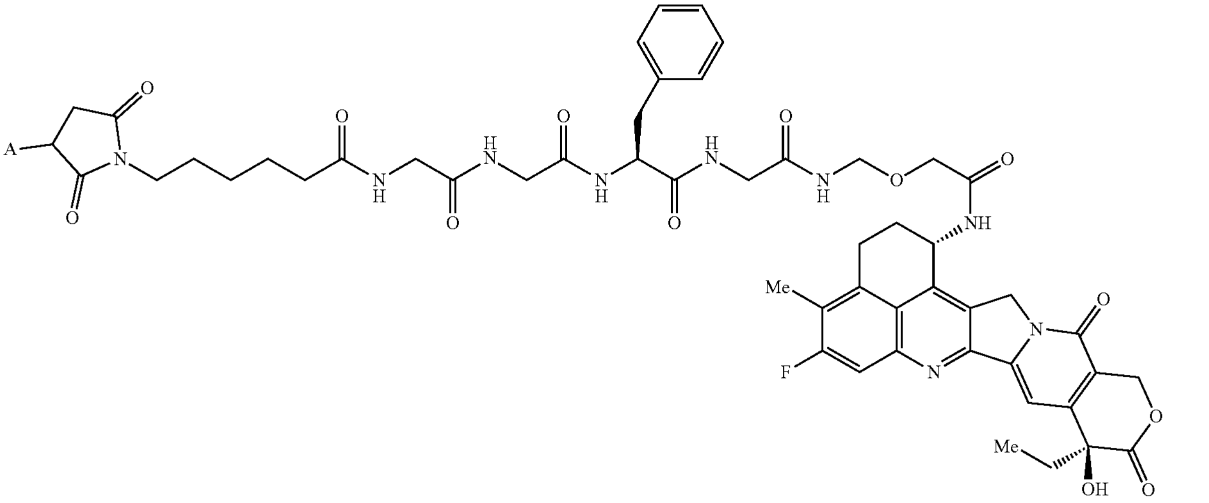

wherein A represents the connecting position to an antibody, is conjugated to an anti-HER2 antibody via a thioether bond.

In another combination embodiment, the anti-HER2 antibody-drug conjugate as defined above for the first combination embodiment is combined with a CDK9 inhibitor which is a compound represented by the following formula (I):

(I)

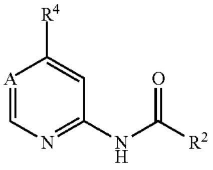

wherein:

A is $C(R^5)$ or N;

$R^5$ is H, $C_{1-3}$ alkyl, CN or halogen;

$R^2$ is 3-7 membered heterocycloalkyl or 3-7 membered cycloalkyl; optionally substituted with one to three substituents independently selected from the group consisting of $R^{10}$, $OR^{10}$, $SR^{10}$, S(O) $R^{10}$, $S(O)_2R^{10}$, $C(O)R^{10}$, C(O) $OR^{10}$, OC(O) $R^{10}$, OC(O) $OR^{10}$, $NH_2$, $NHR^{10}$, $N)(R^{10})_2$, NHC(O)H, NHC(O) $R^{10}$, $NR^{10}C(O)$ H, $NR^{10}C(O)$ $R^{10}$, $NHS(O)_2R^{10}$, $NR^{10}S(O)_2R^{10}$, NHC (O) $OR^{10}$, $NR^{10}C(O)$ $OR^{10}$, NHC(O) $NH_2$, NHC(O) $NHR^{10}$, NHC(O) $N)(R^{10})_2$, $NR^{10}C(O)$ $NH_2$, $NR^{10}C(O)$ $NHR^{10}$, $NR^{10}C(O)$ $N)(R^{10})_2$, C(O) $NH_2$, C(O) $NHR^{10}$, $C(O)N)(R^{10})_2$, C(O)NHOH, $C(O)NHOR^{10}$, C(O) NHS $(O)_2R^{10}$, C(O) $NR^{10}S(O)_2R^{10}$, $S(O)_2NH_2$, $S(O)_2$ $NHR^{10}$, $S(O)_2N(R^{10})_2$, $S(O)_2NHC(O)$ $OR^{10}$, $S(O)_2$ $NR^{10}C(O)$ $OR^{10}$, C(O) H, C(O)OH, OH, CN, $NO_2$, F, Cl, Br and I; wherein one or more ring $CH_2$ groups can optionally be replaced by a corresponding number of —C(O) groups, and one or more ring sulfur or nitrogen atoms may be optionally oxidized to form S-oxides or N-oxides;

$R^{10}$, at each occurrence, is independently selected from the group consisting of a 3 to 6 membered cycloalkyl or heterocycloalkyl group, $C_{1-6}$ alkyl, —O—$C_{1-6}$ alkyl, $C_{1-6}$ alkyl-O—$C_{1-6}$ alkyl, $NH_2$, $C(O)NH_2$, C(O)H, C(O)OH, OH, CN, $NO_2$, F, Cl, Br and I; wherein two $R^{10}$ groups together with the atoms to which they are attached may form a 3 to 6 membered cycloalkyl or heterocycloalkyl group; and each aforementioned $R^{10}$ alkyl, cycloalkyl and heterocycloalkyl group may be further substituted with one or two substituents independently selected from CN, OH, halogen, $C_{1-3}$ alkyl, —O—$C_{1-3}$ alkyl, $NH_2$, NH—$C_{1-3}$ alkyl, and NHC (O)—$C_{1-3}$ alkyl;

$R^4$ is

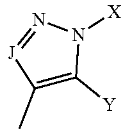

or

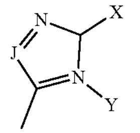

wherein X and Y together with the atoms to which they are attached, form a 5 to 7 membered heterocycloalkyl ring which, in addition to the bridge nitrogen, may contain one or two heteroatoms selected from N, O, and S, which ring may be saturated or partially saturated; wherein one or two ring $CH_2$ groups can optionally be replaced by a corresponding number of —C(O) groups, one or more ring sulfur or nitrogen atoms may be optionally oxidized to form S-oxides or N-oxides and wherein the ring may be substituted on a ring carbon by one or two $R^{10}$ substituents or on a ring nitrogen by an $R^{12}$ substituent;

J is N or $CR^{11}$;

$R^{11}$ is H, $C_{1-3}$ alkyl; and $R^{12}$ is at each occurrence independently selected from the group consisting of a 3 to 6 membered cycloalkyl or heterocycloalkyl group, $C_{1-6}$ alkyl, $C_{1-6}$ alkyl-O—$C_{1-6}$ alkyl, $C(O)NH_2$, O(O)H; wherein each $R^{12}$ alkyl, cycloalkyl and heterocycloalkyl group may be further substituted with one or two substituents independently selected from CN, OH, and halogen, $C_{1-3}$ alkyl, $NH_2$, and NH—$C_{1-3}$ alkyl, NHC(O)—$C_{1-3}$ alkyl, or a pharmaceutical acceptable salt thereof.

In another combination embodiment, the anti-HER2 antibody-drug conjugate as defined above is combined with a CDK9 inhibitor which is a compound represented by formula (I) as defined above wherein, in formula (I), A is $C(R^5)$.

In another combination embodiment, the anti-HER2 antibody-drug conjugate as defined above is combined with a CDK9 inhibitor as defined above wherein, in formula (I), A is $C(R^5)$ and $R^5$ is chloro.

In another combination embodiment, the anti-HER2 antibody-drug conjugate as defined above is combined with a CDK9 inhibitor as defined above wherein, in formula (I), A is $C(R^5)$ and $R^5$ is fluoro.

In another combination embodiment, the anti-HER2 antibody-drug conjugate as defined above is combined with a CDK9 inhibitor as defined above wherein, in formula (I), $R^2$ is a 3-7 membered cycloalkyl.

In another combination embodiment, the anti-HER2 antibody-drug conjugate as defined above is combined with a CDK9 inhibitor as defined above wherein, in formula (I), $R^2$ is 3-7 membered cycloalkyl substituted with $NHCOR^{10}$ or $R^{10}$;

In another combination embodiment, the anti-HER2 antibody-drug conjugate as defined above is combined with a CDK9 inhibitor as defined above wherein, in formula (I), $R^2$ is selected from the group cyclopropyl, cyclobutyl, cyclopentyl, cyclohexyl, and cycloheptyl.

In another combination embodiment, the anti-HER2 antibody-drug conjugate as defined above is combined with a CDK9 inhibitor as defined above wherein, in formula (I), $R^2$ is selected from the cyclopentyl and cyclohexyl.

In another combination embodiment, the anti-HER2 antibody-drug conjugate as defined above is combined with a CDK9 inhibitor as defined above wherein, in formula (I), $R^2$ is cyclohexyl substituted with $NHCOR^{10}$.

In another combination embodiment, the anti-HER2 antibody-drug conjugate as defined above is combined with a CDK9 inhibitor as defined above wherein, in formula (I), $R^2$ is 3-7 membered heterocycloalkyl.

In another combination embodiment, the anti-HER2 antibody-drug conjugate as defined above is combined with a CDK9 inhibitor as defined above wherein, in formula (I), $R^2$ is 3-7 membered heterocycloalkyl substituted with $NHCOR^{10}$.

In another combination embodiment, the anti-HER2 antibody-drug conjugate as defined above is combined with a CDK9 inhibitor as defined above wherein, in formula (I), wherein $R_4$ is

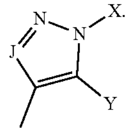

In another combination embodiment, the anti-HER2 antibody-drug conjugate as defined above is combined with a CDK9 inhibitor as defined above wherein $R_4$ is

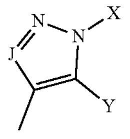

and J is $C(R^{11})$.

In another combination embodiment, the anti-HER2 antibody-drug conjugate as defined above is combined with a CDK9 inhibitor as defined above wherein $R_4$ is

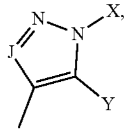

J is $C(R^{11})$, and $R^{11}$ is H.

In another combination embodiment, the anti-HER2 antibody-drug conjugate as defined above is combined with a CDK9 inhibitor as defined above wherein, in formula (I), X and Y together with the atoms to which they are attached form a 5 membered heterocycloalkyl ring.

In another combination embodiment, the anti-HER2 antibody-drug conjugate as defined wherein, in formula (I), X and Y together with the atoms to which they are attached form a 5 membered heterocycloalkyl ring in which one $CH_2$ is substituted with two methyl groups.

In another combination embodiment, the anti-HER2 antibody-drug conjugate as defined above is combined with a CDK9 inhibitor as defined above, wherein the CDK9 inhibitor is AZD4573 represented by the following formula:

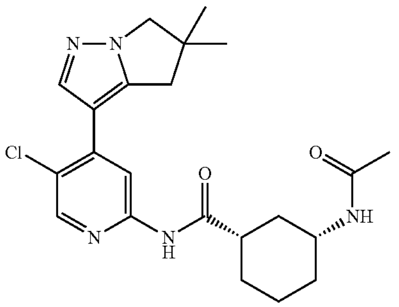

or a pharmaceutically acceptable salt thereof.

In an embodiment of each of the combination embodiments described above, the anti-HER2 antibody comprises a heavy chain comprising CDRH1 consisting of an amino acid sequence represented by SEQ ID NO: 3, CDRH2 consisting of an amino acid sequence represented by SEQ ID NO: 4 and CDRH3 consisting of an amino acid sequence represented by SEQ ID NO: 5, and a light chain comprising CDRL1 consisting of an amino acid sequence represented by SEQ ID NO: 6, CDRL2 consisting of an amino acid sequence consisting of amino acid residues 1 to 3 of SEQ ID NO: 7 and CDRL3 consisting of an amino acid sequence represented by SEQ ID NO: 8. In another embodiment of each of the combination embodiments described above, the anti-HER2 antibody comprises a heavy chain comprising a heavy chain variable region consisting of an amino acid sequence represented by SEQ ID NO: 9 and a light chain comprising a light chain variable region consisting of an amino acid sequence represented by SEQ ID NO: 10. In another embodiment of each of the combination embodiments described above, the anti-HER2 antibody comprises a heavy chain consisting of an amino acid sequence represented by SEQ ID NO: 1 and a light chain consisting of an amino acid sequence represented by SEQ ID NO: 2. In another embodiment of each of the combination embodiments described above, the anti-HER2 antibody comprises a heavy chain consisting of an amino acid sequence represented by SEQ ID NO: 11 and a light chain consisting of an amino acid sequence represented by SEQ ID NO: 2.

In a particularly preferred combination embodiment of the disclosure, the anti-HER2 antibody-drug conjugate is trastuzumab deruxtecan (DS-8201) and the CDK9 inhibitor is the compound represented by the following formula:

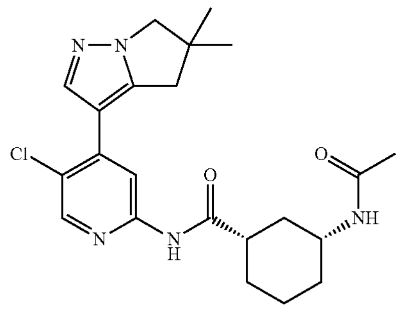 [SMILES: CC(=O)N[C@@H]1CCC[C@H](C(=O)Nc2cc(-c3cnn4c3CC(C)(C)C4)c(Cl)cn2)C1]

also identified as AZD4573.

6. Therapeutic Combined Use and Method

Described in the following are a pharmaceutical product and a therapeutic use and method wherein the anti-HER2 antibody-drug conjugate according to the present disclosure and a CDK9 inhibitor are administered in combination.

The pharmaceutical product and therapeutic use and method of the present disclosure may be characterized in that the anti-HER2 antibody-drug conjugate and the CDK9 inhibitor are separately contained as active components in different formulations, and are administered simultaneously or at different times, or characterized in that the antibody-drug conjugate and the CDK9 inhibitor are contained as active components in a single formulation and administered.

In the pharmaceutical product and therapeutic method of the present disclosure, a single CDK9 inhibitor used in the present disclosure can be administered in combination with the anti-HER2 antibody-drug conjugate, or two or more different CDK9 inhibitors can be administered in combination with the antibody-drug conjugate.

The pharmaceutical product and therapeutic method of the present disclosure can be used for treating cancer, and can be preferably used for treating at least one cancer selected from the group consisting of breast cancer (including triple negative breast cancer and luminal breast cancer), gastric cancer (also called gastric adenocarcinoma), colorectal cancer (also called colon and rectal cancer, and including colon cancer and rectal cancer), lung cancer (including small cell lung cancer and non-small cell lung cancer), esophageal cancer, head-and-neck cancer (including salivary gland cancer and pharyngeal cancer), esophagogastric junction adenocarcinoma, biliary tract cancer (including bile duct cancer), Paget's disease, pancreatic cancer, ovarian cancer, uterine carcinosarcoma, urothelial cancer, prostate cancer, bladder cancer, gastrointestinal stromal tumor, uterine cervix cancer, squamous cell carcinoma, peritoneal cancer, liver cancer, hepatocellular cancer, corpus uteri carcinoma, kidney cancer, vulval cancer, thyroid cancer, penis cancer, leukemia, malignant lymphoma, plasmacytoma, myeloma, glioblastoma multiforme, osteosarcoma, sarcoma, melanoma, acute myeloid leukemia, acute lymphocytic leukemia, high risk myelodysplastic syndrome, chronic myelomonocytic leukemia, Richter's syndrome, B-cell non-Hodgkin lymphoma, T-cell non-Hodgkin lymphoma, small lymphocytic lymphoma, multiple myeloma, chronic lymphocytic leukemia, diffuse large B cell lymphoma, Burkitt's lymphoma, and follicular lymphoma, and can be more preferably used for treating at least one cancer selected from the group consisting of breast cancer, gastric cancer, colorectal cancer, lung cancer (preferably non-small cell lung cancer), pancreatic cancer, ovarian cancer, prostate cancer, and kidney cancer.

The presence or absence of HER2 tumor markers can be determined, for example, by collecting tumor tissue from a cancer patient to prepare a formalin-fixed, paraffin-embedded (FFPE) specimen and subjecting the specimen to a test for gene products (proteins), for example, with an immunohistochemical (IHC) method, a flow cytometer, or Western blotting, or to a test for gene transcription, for example, with an in situ hybridization (ISH) method, a quantitative PCR method (q-PCR), or microarray analysis, or by collecting cell-free circulating tumor DNA (ctDNA) from a cancer patient and subjecting the ctDNA to a test with a method such as next-generation sequencing (NGS).

The pharmaceutical product and therapeutic method of the present disclosure can be used for HER2-expressing cancer, which may be HER2-overexpressing cancer (high or moderate) or may be HER2 low-expressing cancer.

In the present disclosure, the term "HER2-overexpressing cancer" is not particularly limited as long as it is recognized as HER2-overexpressing cancer by those skilled in the art. Preferred examples of the HER2-overexpressing cancer can include cancer given a score of 3+ for the expression of HER2 in an IHC method, and cancer given a score of 2+ for the expression of HER2 in an IHC method and determined as positive for the expression of HER2 in an in situ hybridization method (ISH). The in situ hybridization method of the present disclosure includes a fluorescence in situ hybridization method (FISH) and a dual color in situ hybridization method (DISH).

In the present disclosure, the term "HER2 low-expressing cancer" is not particularly limited as long as it is recognized as HER2 low-expressing cancer by those skilled in the art. Preferred examples of the HER2 low-expressing cancer can include cancer given a score of 2+ for the expression of HER2 in an IHC method and determined as negative for the expression of HER2 in an in situ hybridization method, and cancer given a score of 1+ for the expression of HER2 in an IHC method.

The method for scoring the degree of HER2 expression by the IHC method, or the method for determining positivity or negativity to HER2 expression by the in situ hybridization method is not particularly limited as long as it is recognized by those skilled in the art. Examples of the method can include a method described in the 4th edition of the guidelines for HER2 testing, breast cancer (developed by the Japanese Pathology Board for Optimal Use of HER2 for Breast Cancer).

The cancer, particularly in regard to the treatment of breast cancer, may be HER2-overexpressing (high or moderate) or low-expressing breast cancer, or triple-negative breast cancer, and/or may have a HER2 status score of IHC 3+, IHC 2+, IHC 1+ or IHC>0 and <1+.

The pharmaceutical product and therapeutic method of the present disclosure can be preferably used for a mammal, but are more preferably used for a human.

The antitumor effect of the pharmaceutical product and therapeutic method of the present disclosure can be confirmed by transplanting cancer cells to a test subject animal to prepare a model and measuring reduction in tumor volume or life-prolonging effect by application of the pharmaceutical product and therapeutic method of the present disclosure. And then, the effect of combined use of the antibody-drug conjugate used in the present disclosure and a CDK9 inhibitor can be confirmed by comparing antitumor effect with single administration of the antibody-drug conjugate used in the present disclosure and that of the CDK9 inhibitor.

The antitumor effect of the pharmaceutical product and therapeutic method of the present disclosure can be confirmed in a clinical trial using any of an evaluation method with Response Evaluation Criteria in Solid Tumors (RECIST), a WHO evaluation method, a Macdonald evaluation method, body weight measurement, and other approaches, and can be determined on the basis of indexes of complete response (CR), partial response (PR); progressive disease (PD), objective response rate (ORR), duration of response (DoR), progression-free survival (PFS), overall survival (OS), and so on.

By using the above methods, the superiority in antitumor effect of the pharmaceutical product and therapeutic method of the present disclosure to existing pharmaceutical products and therapeutic methods for cancer treatment can be confirmed.

The pharmaceutical product and therapeutic method of the present disclosure can delay development of cancer cells, inhibit growth thereof, and further kill cancer cells. These effects can allow cancer patients to be free from symptoms caused by cancer or achieve improvement in quality of life (QOL) of cancer patients and attain a therapeutic effect by sustaining the lives of the cancer patients. Even if the pharmaceutical product and therapeutic method of the present disclosure do not accomplish killing cancer cells, they can achieve higher QOL of cancer patients while achieving longer-term survival, by inhibiting or controlling the growth of cancer cells.

The pharmaceutical product of the present disclosure can be expected to exert a therapeutic effect by application as systemic therapy to patients, and additionally, by local application to cancer tissues.

The pharmaceutical product of the present disclosure can be administered containing at least one pharmaceutically suitable ingredient. Pharmaceutically suitable ingredients can be suitably selected and applied from formulation additives or the like that are generally used in the art, in accordance with the dosage, administration concentration, or the like of the antibody-drug conjugate used in the present disclosure and a CDK9 inhibitor. The anti-HER2 antibody-drug conjugate used in the present disclosure can be administered, for example, as a pharmaceutical product containing a buffer such as histidine buffer, a vehicle such as sucrose and trehalose, and a surfactant such as Polysorbates 80 and 20. The pharmaceutical product containing the antibody-drug conjugate used in the present disclosure can be preferably used as an injection, can be more preferably used as an aqueous injection or a lyophilized injection, and can be even more preferably used as a lyophilized injection.

In the case that the pharmaceutical product containing the anti-HER2 antibody-drug conjugate used in the present disclosure is an aqueous injection, the aqueous injection can be preferably diluted with a suitable diluent and then given as an intravenous infusion. Examples of the diluent can include dextrose solution and physiological saline, dextrose solution can be preferably exemplified, and 5% dextrose solution can be more preferably exemplified.

In the case that the pharmaceutical product of the present disclosure is a lyophilized injection, a required amount of the lyophilized injection dissolved in advance in water for injection can be preferably diluted with a suitable diluent and then given as an intravenous infusion. Examples of the diluent can include dextrose solution and physiological saline, dextrose solution can be preferably exemplified, and 5% dextrose solution can be more preferably exemplified.

Examples of the administration route applicable to administration of the pharmaceutical product of the present disclosure can include intravenous, intradermal, subcutaneous, intramuscular, and intraperitoneal routes, and intravenous routes are preferred.

The anti-HER2 antibody-drug conjugate used in the present disclosure can be administered to a human with intervals of 1 to 180 days, can be preferably administered with intervals of a week, two weeks, three weeks, or four weeks, and can be more preferably administered with intervals of three weeks. The anti-HER2 antibody-drug conjugate used in the present disclosure can be administered in a dose of about 0.001 to 100 mg/kg per administration, and can be preferably administered in a dose of 0.8 to 12.4 mg/kg per administration. For example, the anti-HER2 antibody-drug conjugate can be administered once every three weeks at a dose of 0.8 mg/kg, 1.6 mg/kg, 3.2 mg/kg, 5.4 mg/kg, 6.4 mg/kg, 7.4 mg/kg, or 8 mg/kg, and can be preferably administered once every three weeks at a dose of 5.4 mg/kg or 6.4 mg/kg.

The CDK9 inhibitor used in the present disclosure can be administered to a human as an intravenous drip with intervals of 1 to 180 days, and can be preferably administered as an intravenous drip with intervals of a week, two weeks, three weeks, or four weeks. The CDK9 inhibitor used in the present disclosure can be administered as an intravenous drip in a dose of 0.1 mg to 3000 mg per administration, and can be preferably administered as an intravenous drip in a dose of 10 mg to 100 mg per administration, or 1 mg to 20 mg per administration.

The size of the dose required for the therapeutic treatment of a particular disease state will necessarily be varied depending on the subject treated, the route of administration and the severity of the illness being treated. A weekly dose of the CDK9 inhibitor in the range of 0.1-50 mg/kg may be employed. For example, in the case that the CDK9 inhibitor used in the present disclosure is the compound AZD4573 or a pharmaceutically acceptable salt thereof, the CDK9 inhibitor can be preferably intravenously administered once per week in a dose of from 1 mg to 50 mg per administration, for example 3 mg, 6 mg, 9 mg, 12 mg, 15 mg or 18 mg per administration.

The pharmaceutical product and therapeutic method of the present disclosure can be used as adjuvant chemotherapy combined with surgery operation. The pharmaceutical product of the present disclosure may be administered for the purpose of reducing tumor size before surgical operation (referred to as preoperative adjuvant chemotherapy or neoadjuvant therapy), or may be administered for the purpose of preventing recurrence of tumor after surgical operation (referred to as postoperative adjuvant chemotherapy or adjuvant therapy).

EXAMPLES

The present disclosure is specifically described in view of the examples shown below. However, the present disclosure is not limited to these. Further, it is by no means to be interpreted in a limited way.

Example 1: Production of Antibody-Drug Conjugate

In accordance with a production method described in WO2015/115091 and using an anti-HER2 antibody (an antibody comprising a heavy chain consisting of an amino acid sequence represented by SEQ ID NO: 11 (amino acid residues 1 to 449 of SEQ ID NO: 1) and a light chain consisting of an amino acid sequence consisting of all amino acid residues 1 to 214 of SEQ ID NO: 2), an anti-HER2 antibody-drug conjugate in which a drug-linker represented by the following formula:

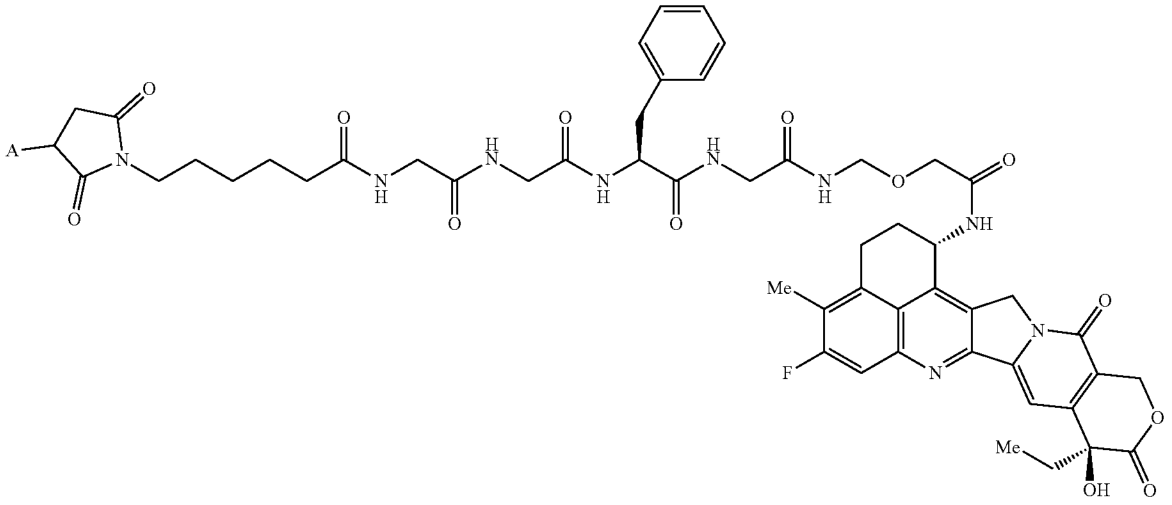

wherein A represents the connecting position to an antibody, is conjugated to the anti-HER2 antibody via a thioether bond was produced (DS-8201: trastuzumab deruxtecan). The DAR of the antibody-drug conjugate is 7.7 or 7.8.

Example 2: Production of CDK9 Inhibitor

In accordance with a production method described in WO2017/001354, a CDK9 inhibitor of formula (I) is prepared. Specifically, (1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide:

(AZD4573)

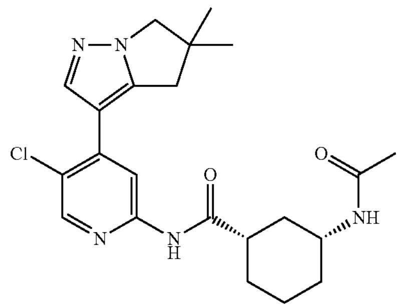 [SMILES: CC(=O)N[C@@H]1CCC[C@H](C(=O)Nc2cc(-c3cnn4c3CC(C)(C)C4)c(Cl)cn2)C1]

can be prepared according to Example 14 of WO2017/001354.

Example 3: Antitumor Test

Combination of antibody-drug conjugate DS-8201 (trastuzumab deruxtecan) with CDK9 inhibitor AZD4573 ((1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide)

Method:

Four HER2 cell lines—three breast cancer (SKBR3, MDA-MB-468, and KPL4) and one gastric cancer (NCI-N87) as shown in Table 1—were treated with either vehicle (DMSO) or three, log-fold increasing concentrations of DS-8201 (3, 30, and 300 ng/mL) for 66 hours at which point either vehicle or a 10-point, ½ log serial dilution of AZD4573 was added for an additional 6 hours.

TABLE 1

| Cell line | HER2 expression | Cancer type |
|---|---|---|
| SKBR3 | Amp/High | Breast (HER2+) |
| MDA-MB-468 | Low | Breast (TNB) |
| KPL4 | High | Breast (HER2+) |
| NCI-N87 | High | Gastric |

Following the 6-hour incubation with AZD4573, both drugs were washed out by removing the media, adding and removing fresh phosphate-buffered saline (PBS) 2 times, and replacing the last wash with fresh culture media. The cells were then incubated for another 18 hours before assessment of cell viability using the CellTiter-Glo reagent. GraphPad Prism was used to generate dose-response curves, as shown in FIG. 12.

Preclinical breast and gastric cancer cell lines show differential activity to DS-8201 across a range of doses, but complete loss of viability is not observed in even the most sensitive of the four cell lines selected for this screen.

In two out of the four cell lines tested (FIG. 12: top row), 6-hour treatment with AZD4573 following 66-hour lead-in of DS-8201 resulted in enhanced loss of cell viability in a dose-dependent manner, thus showing combination benefit.

Accordingly, enhanced loss of viability of preclinical HER2 cancer cell lines has been demonstrated by combination of DS-8201 with acute CDK9 inhibition using AZD4573.

Example 4: Antitumor Test

Combination of antibody-drug conjugate DS-8201 (trastuzumab deruxtecan) with CDK9 inhibitor AZD4573 ((1S,3R)-3-acetamido-N-(5-chloro-4-(5,5-dimethyl-5,6-dihydro-4H-pyrrolo[1,2-b]pyrazol-3-yl)pyridin-2-yl)cyclohexanecarboxamide)

Method:

To evaluate combination efficacy of AZD4573 (CDK9 inhibitor) with DS-8201, 69 CB17-SCID mice were implanted subcutaneously with HCC1954 breast cancer cells (HER2+ cell line). Tumor volume was monitored via caliper measurements, and mice were randomized based on mean tumor size. Upon randomization, groups being treated with DS-8201 were dosed intravenously. AZD4573 was given 24 hours after DS-8201 treatment. All AZD4573 doses were administered IP, 2 hours apart. A BID regimen was used for 10 mg/kg dose, and TID was used for 5 mg/kg dose. AZD4573 dosing was given weekly thereafter for a total of 3 cycles. Thus, DS-8201 was administered via IV on Day 0, and AZD4573 treatments were given on Days 1, 8, and 15, as indicated by the vertical dotted lines in FIG. 13.

Results:

Tumor volumes for treatments with DS-8201 and/or AZD4573 are shown in FIG. 13. Data represents change in tumor volume over time for treatment groups. Tumor growth inhibition (TGI) of tumor measurements was calculated in relation to Vehicle control, as shown in Table 2:

TABLE 2

| Treatment | % TGI |
|---|---|
| DS-8201: 3 mg/kg (mpk) | 91.867 |
| DS-8201: 3 mg/kg (mpk) + AZD4573: 10 mg/kg (mpk) | 96.441 |

TABLE 2-continued

| Treatment | % TGI |
|---|---|
| DS-8201: 10 mg/kg (mpk) | 99.573 |
| DS-8201: 10 mg/kg (mpk) + AZD4573: 10 mg/kg (mpk) | 99.829 |
| DS-8201: 10 mg/kg (mpk) + AZD4573: 5 mg/kg (mpk) | 99.776 |

Tumor kinetic growth curves (FIG. 13) and TGI analysis (Table 2) show that AZD4573 exhibited minimal tumor growth control as monotherapy in the HCC1954 model. DS-8201 monotherapy treatment at 3 mg/kg resulted in 91.867% TGI, and at 10 mg/kg in 96.441% TGI. The most robust response was observed in DS-8201 10 mg/kg treated groups combined with AZD4573 10 mg/kg and 5 mg/kg (99.829% TGI and 99.776% TGI, respectively), with best activity was observed with DS-8201 at 10 mg/kg+AZD4573 at 10 mg/kg BID (99.829% TGI).

The foregoing written specification is considered to be sufficient to enable one skilled in the art to practice the embodiments. The foregoing description and Examples detail certain embodiments and describe the best mode contemplated by the inventors. It will be appreciated, however, that no matter how detailed the foregoing may appear in text, the embodiments may be practiced in many ways and the claims include any equivalents thereof.

Free Text of Sequence Listing

SEQ ID NO: 1—Amino acid sequence of a heavy chain of an anti-HER2 antibody

SEQ ID NO: 2—Amino acid sequence of a light chain of an anti-HER2 antibody

SEQ ID NO: 3—Amino acid sequence of a heavy chain CDRH1 [=amino acid residues 26 to 33 of SEQ ID NO: 1]

SEQ ID NO: 4—Amino acid sequence of a heavy chain CDRH2 [=amino acid residues 51 to 58 of SEQ ID NO: 1]

SEQ ID NO: 5—Amino acid sequence of a heavy chain CDRH3 [=amino acid residues 97 to 109 of SEQ ID NO: 1]

SEQ ID NO: 6—Amino acid sequence of a light chain CDRL1 [=amino acid residues 27 to 32 of SEQ ID NO: 2]

SEQ ID NO: 7—Amino acid sequence comprising an amino acid sequence of a light chain CDRL2 (SAS) [=amino acid residues 50 to 56 of SEQ ID NO: 2]

SEQ ID NO: 8—Amino acid sequence of a light chain CDRL3 [=amino acid residues 89 to 97 of SEQ ID NO: 2]

SEQ ID NO: 9—Amino acid sequence of a heavy chain variable region [=amino acid residues 1 to 120 of SEQ ID NO: 1]

SEQ ID NO: 10—Amino acid sequence of a light chain variable region [=amino acid residues 1 to 107 of SEQ ID NO: 2]

SEQ ID NO: 11—Amino acid sequence of a heavy chain [=amino acid residues 1 to 449 of SEQ ID NO: 1]

The invention claimed is:

1. A pharmaceutical product comprising an anti-HER2 antibody-drug conjugate and AZD4573, which is represented by the following formula:

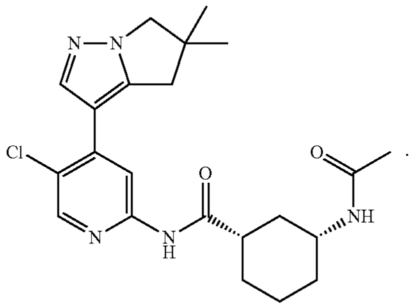 [SMILES: CC(=O)N[C@@H]1CCC[C@H](C(=O)Nc2cc(-c3cnn4c3CC(C)(C)C4)c(Cl)cn2)C1]

or a pharmaceutically acceptable salt thereof for administration in combination, wherein the anti-HER2 antibody-drug conjugate is an antibody-drug conjugate in which a drug-linker represented by the following formula:

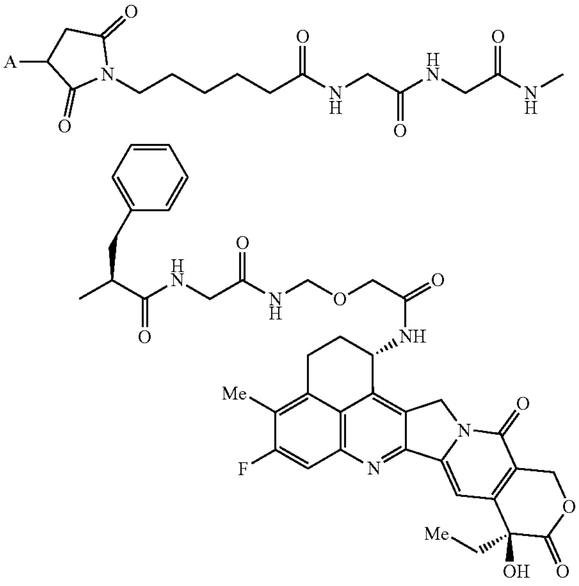

wherein A represents the connecting position to an antibody, is conjugated to an anti-HER2 antibody via a thioether bond and wherein the anti-HER2 antibody is an antibody comprising a heavy chain comprising CDRH1 consisting of an amino acid sequence represented by SEQ ID NO: 3, CDRH2 consisting of an amino acid sequence represented by SEQ ID NO: 4 and CDRH3 consisting of an amino acid sequence represented by SEQ ID NO: 5, and a light chain comprising CDRL1 consisting of an amino acid sequence represented by SEQ ID NO: 6, CDRL2 consisting of an amino acid sequence consisting of amino acid residues 1 to 3 of SEQ ID NO: 7 and CDRL3 consisting of an amino acid sequence represented by SEQ ID NO: 8.

2. The pharmaceutical product according to claim 1, wherein the anti-HER2 antibody is an antibody comprising a heavy chain comprising a heavy chain variable region consisting of an amino acid sequence represented by SEQ ID NO: 9 and a light chain comprising a light chain variable region consisting of an amino acid sequence represented by SEQ ID NO: 10.

3. The pharmaceutical product according to claim 1, wherein the anti-HER2 antibody is an antibody comprising a heavy chain consisting of an amino acid sequence represented by SEQ ID NO: 1 and a light chain consisting of an amino acid sequence represented by SEQ ID NO: 2.

4. The pharmaceutical product according to claim 1, wherein the anti-HER2 antibody is an antibody comprising a heavy chain consisting of an amino acid sequence represented by SEQ ID NO: 11 and a light chain consisting of an amino acid sequence represented by SEQ ID NO: 2.

5. The pharmaceutical product according to claim 1, wherein the anti-HER2 antibody-drug conjugate is represented by the following formula:

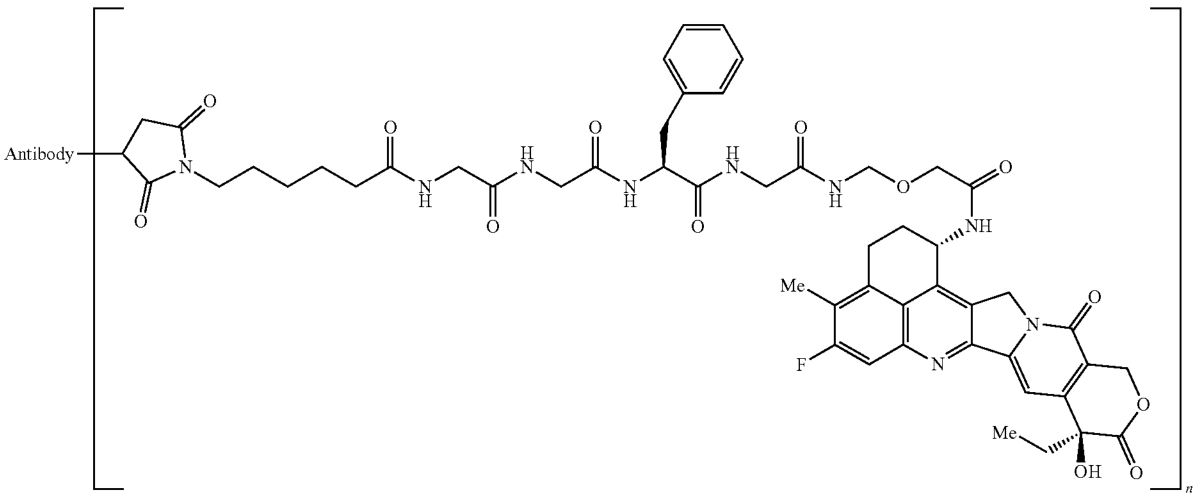

wherein 'Antibody' indicates the anti-HER2 antibody conjugated to the drug-linker via a thioether bond, and n indicates an average number of units of the drug-linker conjugated per antibody molecule in the antibody-drug conjugate, wherein n is in the range of from 7 to 8.

6. The pharmaceutical product according to claim 1, wherein the anti-HER2 antibody-drug conjugate is trastuzumab deruxtecan.

7. The pharmaceutical product according to claim 1, wherein the product is a composition comprising the anti-HER2 antibody-drug conjugate and AZD4573 or pharmaceutically acceptable salt thereof, for simultaneous administration.

8. The pharmaceutical product according to claim 1, wherein the product is a combination of a composition comprising the anti-HER2 antibody-drug conjugate and a separate composition comprising AZD4573 or pharmaceutically acceptable salt thereof, for sequential or simultaneous administration.

9. A method of treating cancer comprising administering to a subject in need thereof a combination of an anti-HER2 antibody-drug conjugate and AZD4573, which is represented by the following formula:

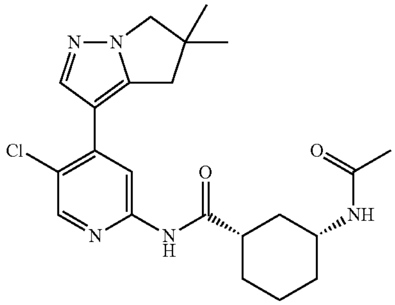

, or a pharmaceutically acceptable salt thereof, wherein the anti-HER2 antibody-drug conjugate is an antibody-drug conjugate in which a drug-linker represented by the following formula:

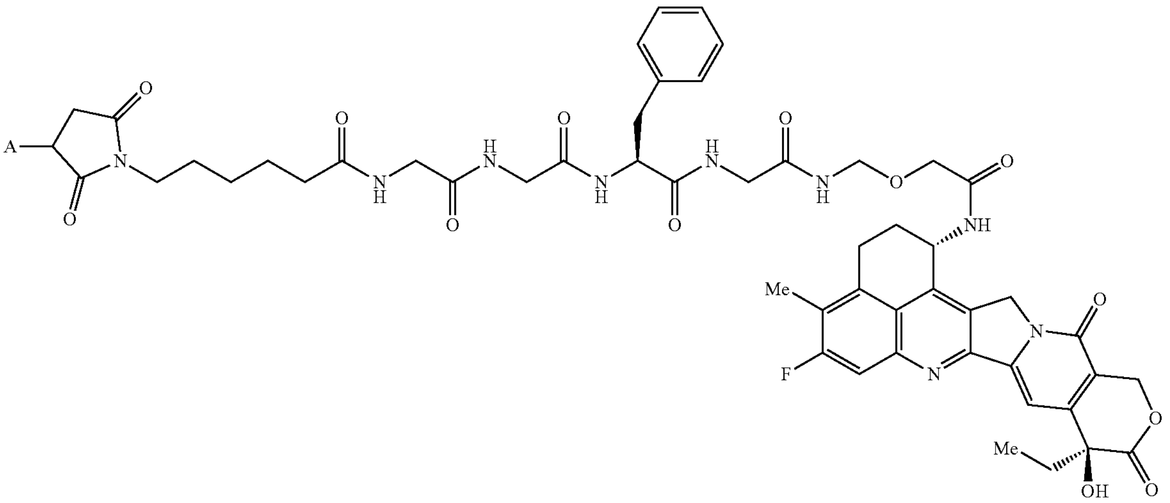

wherein A represents the connecting position to an antibody, is conjugated to an anti-HER2 antibody via a thioether bond and wherein the anti-HER2 antibody is an antibody comprising a heavy chain comprising CDRH1 consisting of an amino acid sequence represented by SEQ ID NO: 3, CDRH2 consisting of an amino acid sequence represented by SEQ ID NO: 4 and CDRH3 consisting of an amino acid sequence represented by SEQ ID NO: 5, and a light chain comprising CDRL1 consisting of an amino acid sequence represented by SEQ ID NO: 6, CDRL2 consisting of an amino acid sequence consisting of amino acid residues 1 to 3 of SEQ ID NO: 7 and CDRL3 consisting of an amino acid sequence represented by SEQ ID NO: 8.

10. The method according to claim 9, wherein the cancer is breast cancer.

11. The method according to claim 9, wherein the cancer is gastric cancer.

12. The method according to claim 9, wherein the method comprises administering the anti-HER2 antibody-drug conjugate and AZD4573 or pharmaceutically acceptable salt thereof sequentially.

13. The method according to claim 9, wherein the method comprises administering the anti-HER2 antibody-drug conjugate and AZD4573 or pharmaceutically acceptable salt thereof simultaneously.

14. The method according to claim 9, wherein the anti-HER2 antibody-drug conjugate is represented by the following formula:

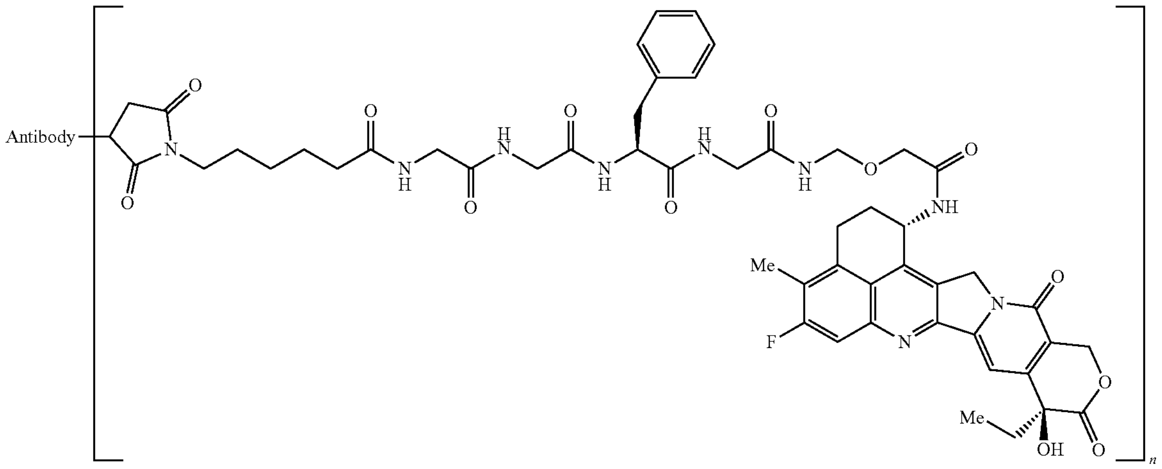

wherein 'Antibody' indicates the anti-HER2 antibody conjugated to the drug-linker via a thioether bond, and n indicates an average number of units of the drug-linker conjugated per antibody molecule in the anti-body-drug conjugate;

wherein the anti-HER2 antibody is an antibody comprising a heavy chain comprising a heavy chain variable region consisting of an amino acid sequence represented by SEQ ID NO: 9 and a light chain comprising a light chain variable region consisting of an amino acid sequence represented by SEQ ID NO: 10, and wherein n is in the range of from 7 to 8.

15. The method according to claim 9, wherein the anti-HER2 antibody-drug conjugate is trastuzumab deruxtecan.

16. The method according to claim 10, wherein the breast cancer has a HER2 status score of IHC 3+.

17. The method according to claim 10, wherein the breast cancer is HER2 low-expressing breast cancer.

18. The method according to claim 10, wherein the breast cancer has a HER2 status score of IHC 2+.

19. The method according to claim 10, wherein the breast cancer has a HER2 status score of IHC 1+.

20. The method according to claim 10, wherein the breast cancer has a HER2 status score of IHC>0 and <1+.

21. The method according to claim 10, wherein the breast cancer is triple-negative breast cancer.

22. The method according to claim 14, wherein the anti-HER2 antibody is an antibody comprising i) a heavy chain consisting of an amino acid sequence represented by SEQ ID NO: 1 and a light chain consisting of an amino acid sequence represented by SEQ ID NO: 2; or ii) a heavy chain consisting of an amino acid sequence represented by SEQ ID NO: 11 and a light chain consisting of an amino acid sequence represented by SEQ ID NO: 2.

* * * * *